United States Patent
Napolitano et al.

(10) Patent No.: US 6,193,663 B1
(45) Date of Patent: Feb. 27, 2001

(54) DIAGNOSTIC ULTRASOUND IMAGING METHOD AND SYSTEM WITH IMPROVED FRAME RATE

(75) Inventors: David J. Napolitano, Pleasanton; Christopher R. Cole, Redwood City; Gregory L. Holley, Mountain View, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/282,396

(22) Filed: Mar. 31, 1999

Related U.S. Application Data

(63) Continuation-in-part of application No. 09/198,219, filed on Nov. 23, 1998, now abandoned, which is a continuation-in-part of application No. 08/993,395, filed on Dec. 18, 1997, now abandoned, and a continuation-in-part of application No. 08/993,533, filed on Dec. 18, 1997, now abandoned.

(51) Int. Cl.[7] .................................................. A61B 8/00
(52) U.S. Cl. ................................................... 600/447
(58) Field of Search ................................. 600/443, 447, 600/458; 73/625–626; 367/311, 103–105

(56) References Cited

U.S. PATENT DOCUMENTS

| | | |
|---|---|---|
| 4,561,019 | 12/1985 | Lizzi et al. . |
| 4,886,069 | 12/1989 | O'Donnell . |
| 4,887,306 | 12/1989 | Hwang et al. . |
| 4,896,283 | 1/1990 | Pesque . |
| 5,010,885 | 4/1991 | Fink et al. . |
| 5,431,167 | 7/1995 | Savord . |
| 5,476,098 | 12/1995 | O'Donnell . |
| 5,549,111 | 8/1996 | Wright et al. . |
| 5,617,862 | 4/1997 | Cole et al. . |
| 5,623,928 | 4/1997 | Wright et al. . |
| 5,632,277 | 5/1997 | Chapman et al. . |
| 5,642,329 | 6/1997 | Zehner . |
| 5,667,373 | 9/1997 | Wright et al. . |
| 5,706,819 | 1/1998 | Hwang et al. . |
| 5,833,613 | 11/1998 | Averkiou et al. . |
| 6,016,285 | 1/2000 | Wright et al. . |
| 6,066,099 | 5/2000 | Thomenius et al. . |

FOREIGN PATENT DOCUMENTS 0 770 352 A1   5/1997   (EP) .

OTHER PUBLICATIONS

"Coded Excitation for Hamonics Imaging, "Y. Takeuchi, 1996, IEEE UTS Symp. pp. 1433–1436.

Primary Examiner—Francis J. Jaworski
(74) Attorney, Agent, or Firm—Brinks Hofer Gilson & Lione

(57) ABSTRACT

A medical diagnostic ultrasonic imaging system acquires receive beams from spatially distinct transmit beams. The receive beams alternate in type between at least first and second types across the region being imaged. The first and second types of receive beams differ in at least one scan parameter other than transmit and receive line geometry, and can for example differ in transmit phase, transmit or receive aperture, system frequency, transmit focus, complex phase angle, transmit code or transmit gain. Receive beams associated with spatially distinct ones of the transmit beams (including at least one beam of the first type and at least one beam of the second type) are then combined. In this way, many two-pulse techniques, including, for example, phase inversion techniques, synthetic aperture techniques, synthetic frequency techniques, and synthetic focus techniques, can be used while substantially reducing the frame rate penalty normally associated with such techniques.

61 Claims, 18 Drawing Sheets

TRANSMIT APERTURE
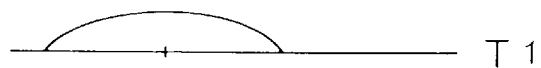
T1
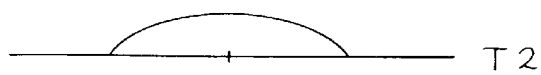
T2
T3
Fig. 14
RECEIVE APERTURE
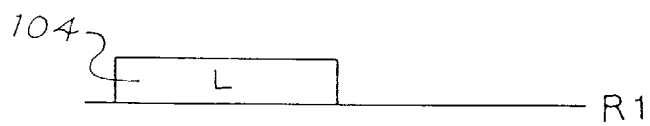
R1
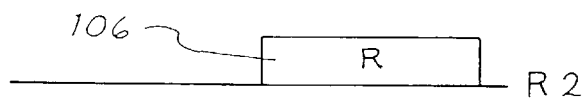
R2
R3
Fig. 15
RECEIVE APERTURE
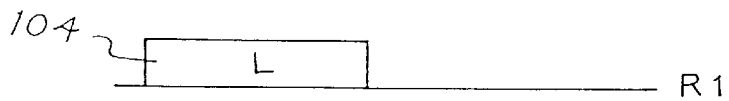
R1
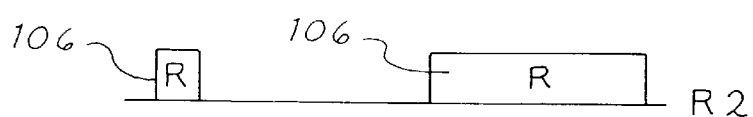
R2
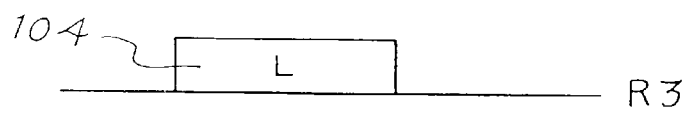
R3
Fig. 16

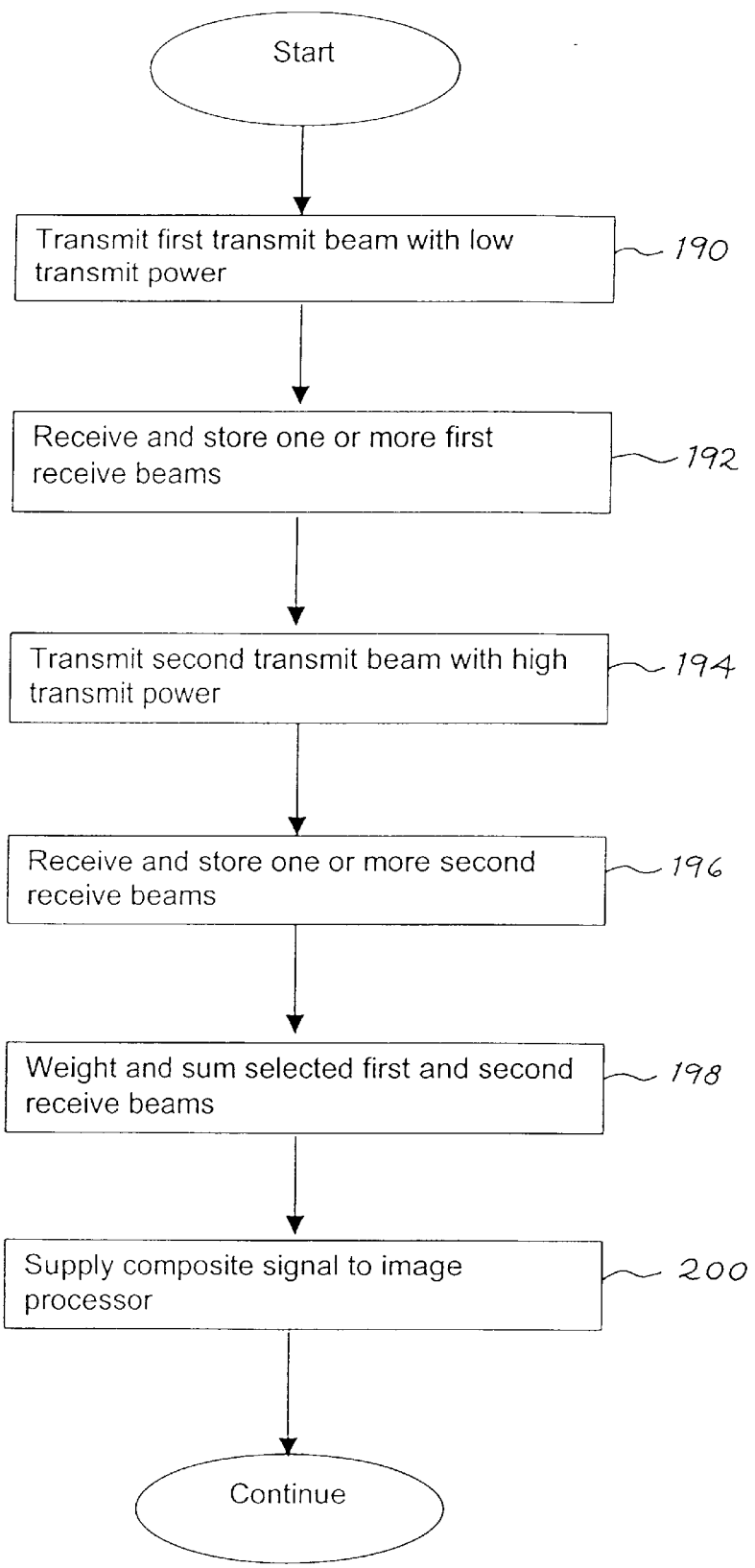

|  |  | Wa = 2, Wb = -1 | Wa = 4, Wb = -1 |
|---|---|---|---|
| SCAN LINE | TX GAIN | COMPOSITE SIGNAL | COMPOSITE SIGNAL |
| 1 | 1 | HARMONIC | FUNDAMENTAL |
| 2 | 2 | HARMONIC | FUNDAMENTAL |
| 3 | 1 | HARMONIC | FUNDAMENTAL |
| 4 | 2 | HARMONIC | FUNDAMENTAL |

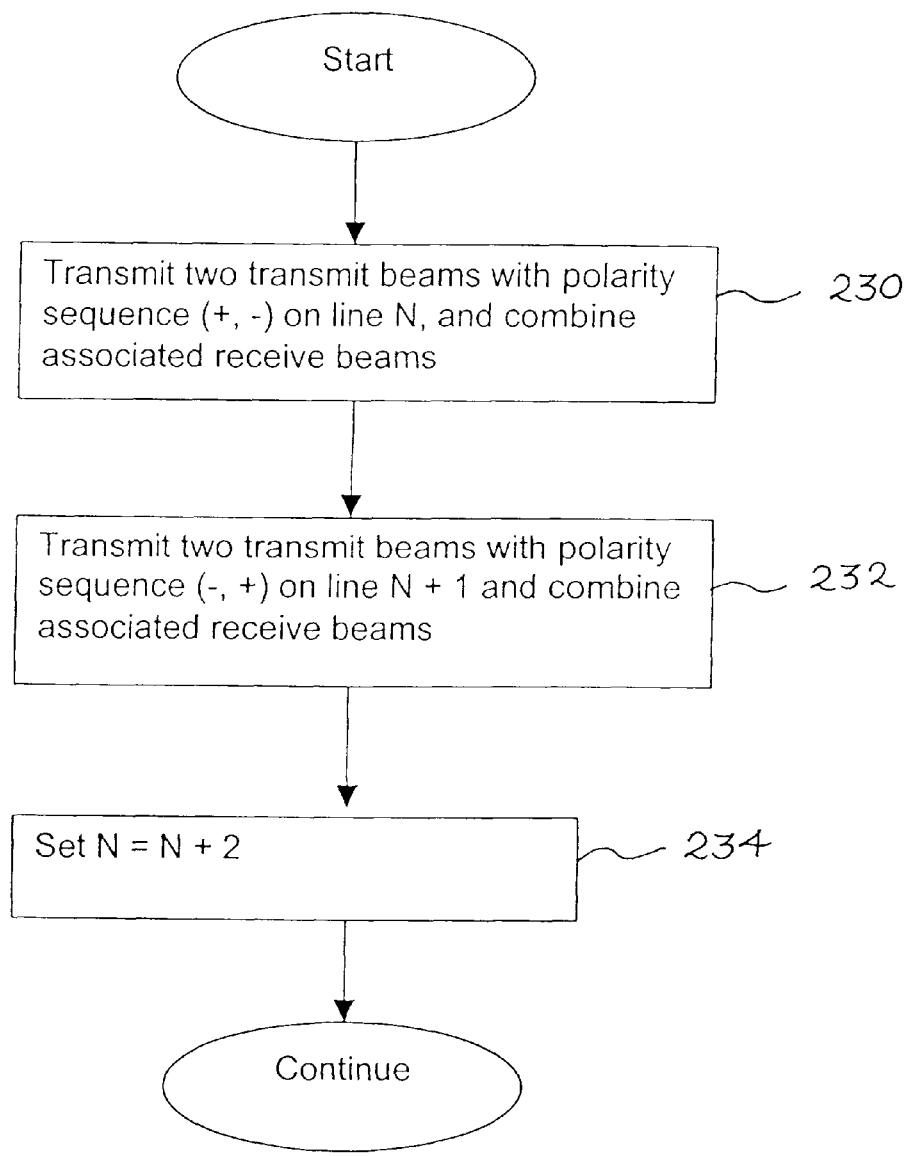

DIAGNOSTIC ULTRASOUND IMAGING METHOD AND SYSTEM WITH IMPROVED FRAME RATE

RELATED APPLICATIONS

This application is a continuation-in-part of U.S. patent application Ser. No. 09/198,219, filed Nov. 23, 1998 and now abandoned, which is in turn a continuation-in-part of U.S. patent application Ser. No. 08/993,395, filed Dec. 18, 1997, and U.S. patent application Ser. No. 08/993,533, filed Dec. 18, 1997 both now abandoned. All three of these related U.S. patent applications are hereby incorporated by reference in their entirety.

BACKGROUND OF THE INVENTION

This invention relates to medical diagnostic ultrasonic imaging methods and systems, and in particular to improvements to such systems that allow an increased frame rate.

In various medical diagnostic ultrasonic imaging applications, multiple transmit beams are fired along the same ultrasound line. Examples of such applications include two-pulse techniques that use phase inversion subtraction to enhance harmonic image components, synthetic aperture techniques, synthetic spectrum techniques, and sequential focus techniques.

The requirement for multiple transmit pulse firings on each ultrasound line results in a substantial reduction in frame rate.

For example, Chapman U.S. Pat. No. 5,632,277 discloses an ultrasound imaging system that employs phase inversion subtraction to enhance the image. In the disclosed system, two transmit ultrasonic pulses which differ in phase by 180° are focused in the same beam direction. The echo signals associated with these pulses are stored and then summed. Linear echoes destructively interfere in this summation due to the 180° phase difference between the two transmitted ultrasonic pulses. Non-linear echoes do not destructively interfere to the same extent, because the phases associated with non-linear echoes no longer differ by 180°. In this way, the amplitude of the non-linear echoes can be increased relative to the amplitude of the linear echoes in the summed signal.

The system disclosed in the Chapman patent suffers from the disadvantage that two ultrasonic pulses must be directed along each beam direction, and this requirement reduces the frame rate by a factor of two.

Similarly, Cole U.S. Pat. No. 5,617,862 discusses a system that coherently sums receive beams along the same steering direction to achieve a synthetic aperture. The disclosed system also results in a substantial reduction in frame rate.

The reductions in frame rate discussed above are inevitable in the disclosed systems, and in many cases the frame rate may fall to clinically unacceptable levels. Additionally, the multiple firing techniques discussed above reduce frame rate in discrete steps. For example, when two transmit beam firings are required for each transmit beam direction, the frame rate is reduced by a factor of two as compared to conventional single transmit beam operation. It would be advantageous to have a technique whereby a continuous trade off could be made between selected performance factors and the resulting frame rate when employing various multiple-pulse modes of operation.

SUMMARY

By way of introduction, preferred embodiments described below transmit a plurality of spatially distinct ultrasonic transmit beams into a region. A plurality of receive beams are received from the region, each receive beam associated with a respective one of the transmit beams. The transmit and receive beams include beams of at least first and second types. The first and second types of beams differ in at least one scan parameter other than transmit and receive line geometry, and can for example differ in transmit waveform, receive spectral response phase, aperture, frequency, focus, gain code, complex phase angle, or alternate polarity sequence. Receive beams associated with spatially distinct ones of the transmit beams (including at least one beam of the first type and at least one beam of the second type) are then preferably combined, either in a coherent manner prior to detection or in a compounding operation subsequent to detection.

Preferably, the first and second types of beams alternate on a line-by-line or group-of-lines by group-of-lines basis. It is the combination that synthesizes the desired feature such as two-pulse cancellation, synthetic aperture, synthetic spectrum, or multiple focus. This approach allows a continuous tradeoff between performance and frame rate by adjustment of the scan line density. For example, if the same scan line density is used in both the normal mode and one of the alternating line modes described above, there is no frame rate loss.

The present invention is defined by the following claims, and nothing in this section should be taken as a limitation on those claims.

BRIEF DESCRIPTION OF THE DRAWINGS

FIG. 14 is a schematic diagram showing transmit apertures utilized in an alternating line aperture embodiment of this invention.

FIGS. 15–19 are schematic diagrams showing receive apertures used in various alternating line aperture embodiments of this invention.

FIG. 25 is a flowchart showing an alternating line transmit gain embodiment of this invention.

FIG. 30 is a flowchart of an alternating line polarity sequence embodiment of this invention.

DETAILED DESCRIPTION OF THE PRESENTLY PREFERRED EMBODIMENTS

The present invention can take many forms, including the specific examples presented in the following sections.

Alternating Line Phase Embodiments

Figure 1:
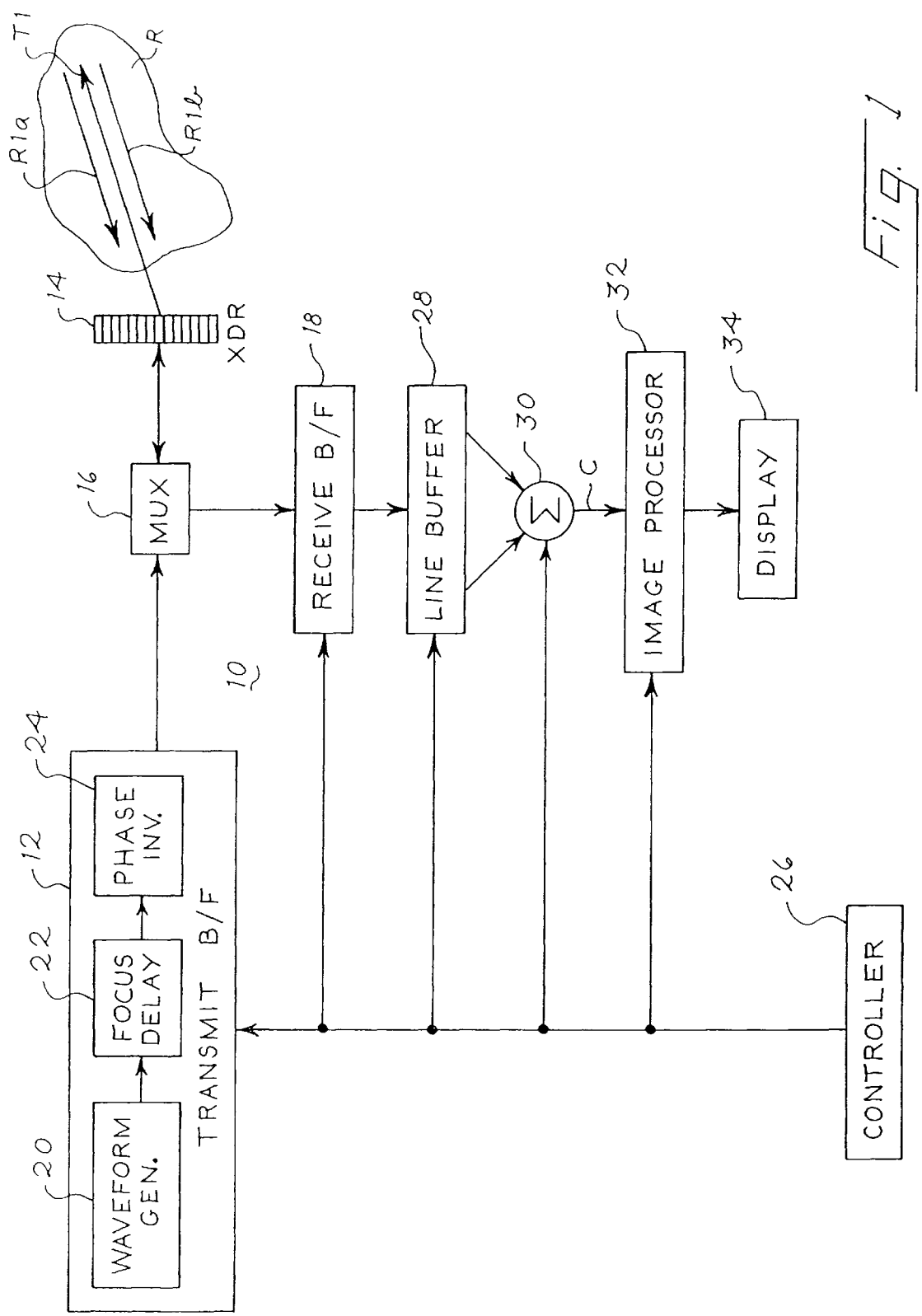
FIG. 1 is a block diagram of an ultrasonic imaging system that incorporates a presently preferred embodiment of this invention.

Referring now to the drawings, FIG. 1 shows a schematic view of an ultrasonic imaging system 10 that incorporates a presently preferred embodiment of this invention that provides alternating line phase. The system 10 includes a transmit beamformer 12 that is coupled to a phased array transducer 14 by a multiplexer 16. The multiplexer 16 also couples the transducer 14 to a receive beamformer 18.

The transmit beamformer 12 in part operates as a conventional transmit beamformer to generate a set of transmit signals for the individual transducers included in the transducer 14. For example, the transmit beamformer 12 can include a waveform generator 20 that applies a suitably shaped ultrasonic pulse to a focus delay 22. The focus delay 22 provides conventional steering delays by any suitable combination of delays, phase shifts and phase rotations. The focus delays are selected to cause ultrasonic signals from the transducer 14 to constructively interfere at a selected transmit focus along a selected transmit beam direction. In FIG. 1, an exemplary transmit beam T1 is shown.

The transmit beamformer 12 additionally includes a phase inverter 24 that is controlled by a controller 26. In this example, the phase inverter 24 is active only for every other transmit beam. Thus, transmit beams T1, T3, T5, . . . are transmitted with positive polarity, and transmit beams T2, T4, T6, . . . are transmitted with inverted or negative polarity.

The receive beamformer 18 can operate in a single beam mode, in which a single receive beam is acquired for each transmit beam, or in a multiple receive beam mode, in which multiple receive beams are acquired in association with each transmit beam. Typically, in the single receive beam mode each receive beam is spatially aligned with the associated transmit beam, while in the multiple receive beam mode each of the receive beams is spatially offset from the respective transmit beam. In FIG. 1, two receive beams R1$a$ and R1$b$ are shown in association with the transmit beam T1. As shown in FIG. 1, the transmit beams including the transmit beam T1 are directed into a region R of the subject, and the receive beams R1$a$, R1$b$ are associated with echoes from the region R.

The receive beamformer 18 applies appropriate delays and phase rotations to coherently sum receive signals from the transducer 14 to create the desired receive beams along desired directions. These receive beams are applied to a line buffer 28 that stores the receive beams for further processing. In this embodiment, the line buffer 28 stores the receive beams coherently. That is, sufficient timing or phase information is preserved, or sufficient phase corrections were made, to allow the interference effects discussed below to be obtained consistently.

Selected receive beams associated with multiple, spatially distinct transmit beams are applied to a summer 30 for summation to form a composite signal C that is applied to an image processor 32. The image processor 32 forms a conventional image such as a B mode image and presents this image on a display 34.

Figure 2:
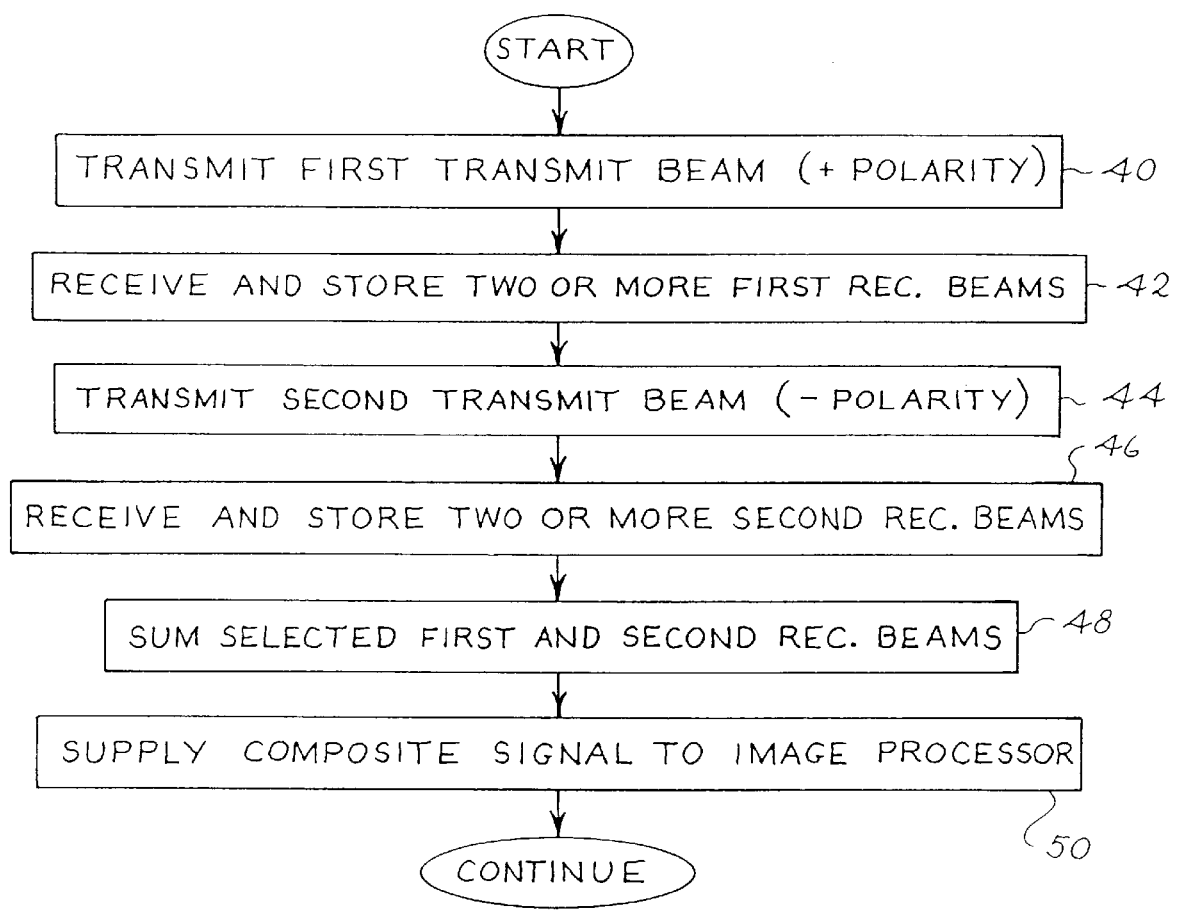
FIG. 2 is a flowchart of a portion of a method practiced by the system of FIG. 1.

FIG. 2 provides a flowchart of a portion of a method practiced by the system of FIG. 1. The system transmits a first transmit beam of positive polarity in a first direction in step 40, and receives and stores one or more first receive beams associated with this first transmit beam in step 42. Then the transmit beamformer transmits a second transmit beam of negative polarity in a second direction in step 44. The second transmit beam is usually adjacent to the first transmit beam. One or more second receive beams associated with the second transmit beam are received and stored in step 46, and selected ones of the first and second receive beams are summed in step 48 to generate a composite signal, which is supplied to the image processor in step 50.

Figure 3:
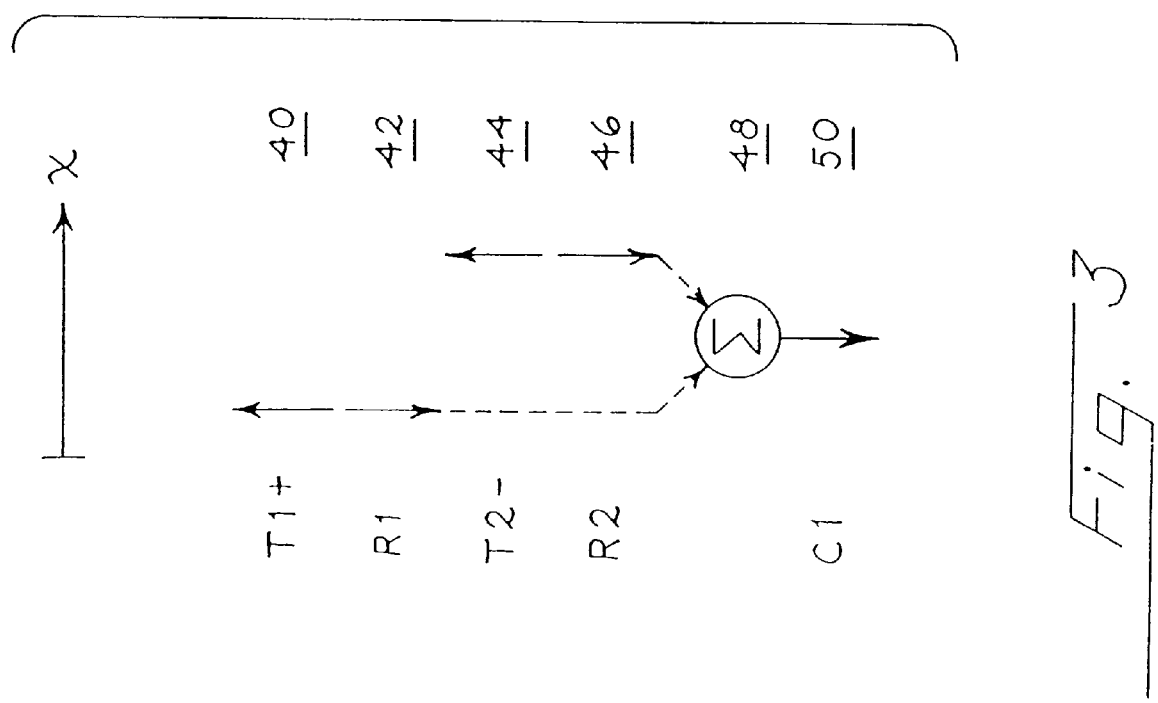

FIG. 3 illustrates the method of FIG. 2 diagrammatically. In FIG. 3 the X direction proceeds from left to right, and transmit and receive beams of differing azimuthal positions are plotted at differing X coordinates. Reference numerals 40–50 have been used in FIG. 3 to designate portions of FIG. 3 that correspond to the correspondingly numbered steps of FIG. 2. Note that the first and second receive beams R1, R2 that are summed in step 48 are associated with spatially distinct transmit beams T1 (positive polarity) and T2 (negative polarity), respectively.

Figure 4:
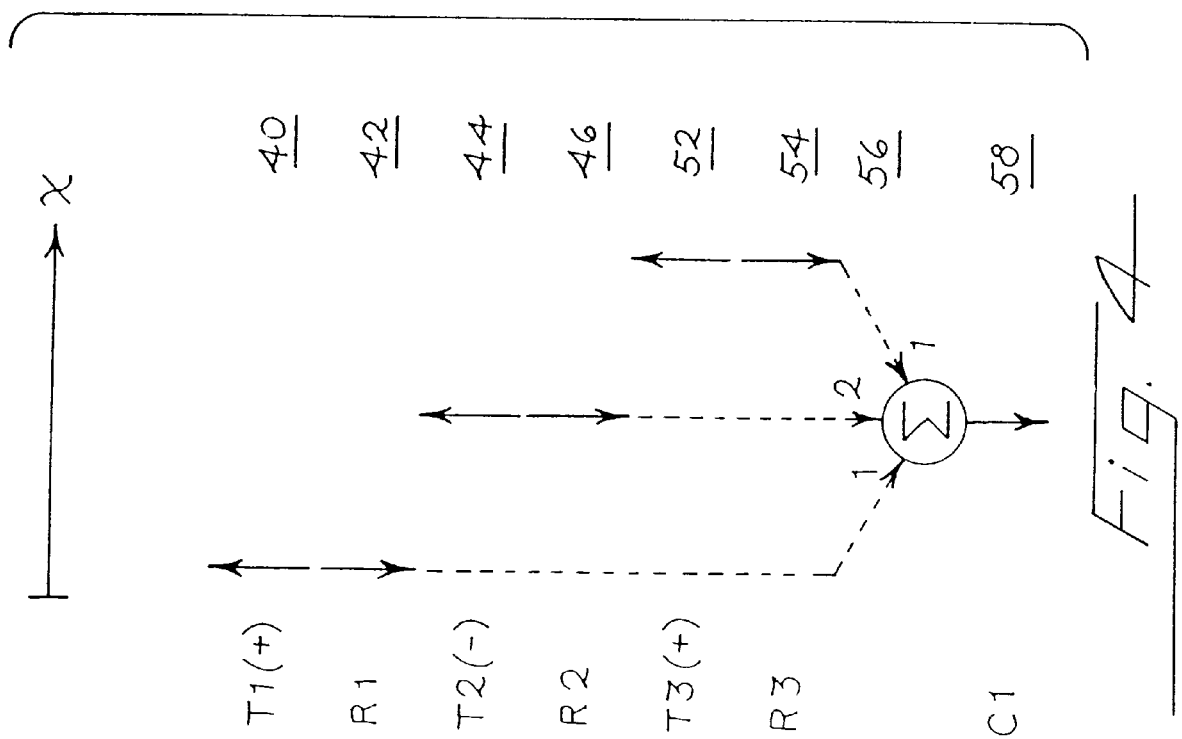
FIGS. 3 and 4 are schematic diagrams illustrating the formation of a composite signal in two alternative embodiments in which a single receive beam is acquired for each transmit beam.

FIG. 4 shows another embodiment of the method of this invention which includes steps 40–46 as described above. In this embodiment, a third transmit beam T3 (positive polarity) is transmitted along a third spatially distinct direction in step 52, and a corresponding receive beam R3 is acquired in step 54. Thus, the receive beams R1, R2, R3 are all aligned with the corresponding transmit beams T1, T2, T3 and are all spatially distinct. These three receive beams R1, R2, R3 are summed in step 56 using summing values [1, 2,1] as shown in FIG. 4 to generate a composite signal C1 that is applied to the image processor in step 58.

Figure 5:
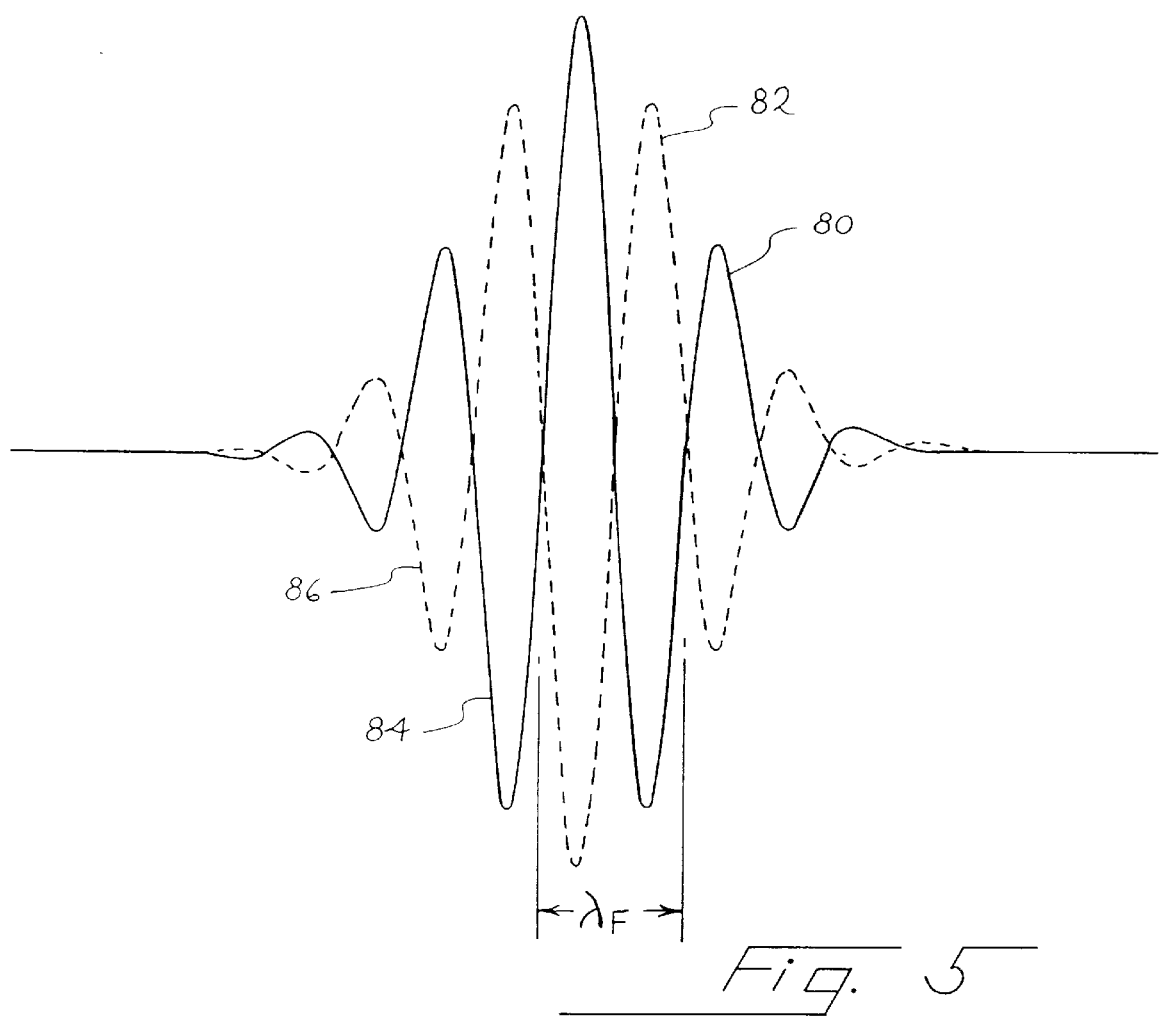
FIGS. 5 through 8 are waveform diagrams illustrating the operation of the method shown in FIG. 3.
Figure 24:
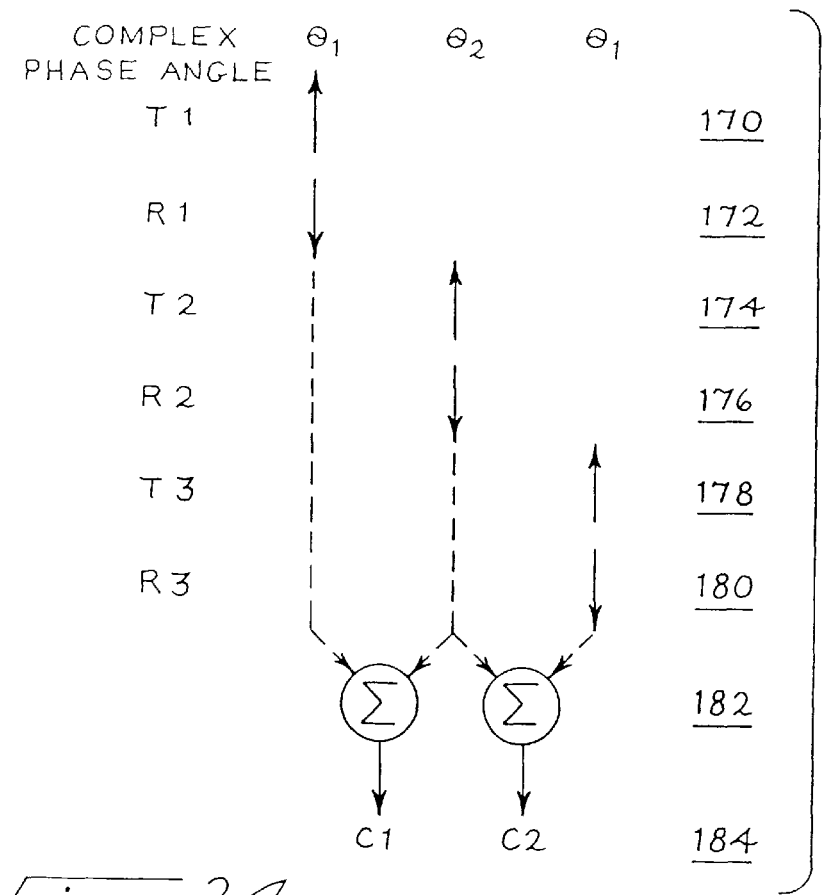
FIG. 24 is a schematic diagram showing an alternating line complex phase angle embodiment of this invention.

FIGS. 5–8 diagrammatically illustrate the benefits obtained with the methods of FIGS. 24. FIG. 5 shows the ultrasonic waveform associated with the positive polarity transmit beams T1, T3 in solid lines and the inverted or negative polarity ultrasonic waveform associated with transmit pulse T2 in dotted lines. As shown in FIG. 5, the inverted polarity pulse differs from the positive polarity pulse by phase inversion or a phase shift of 180°. The ultrasonic pulse shown in FIG. 5 is an amplitude modulated sinusoid, and the sinusoid has a fundamental wavelength $\lambda_F$. Thus, the pulses shown in FIG. 5 represent the fundamental components 80, 82 of the transmit beams T1 and T2, respectively.

Figure 6:
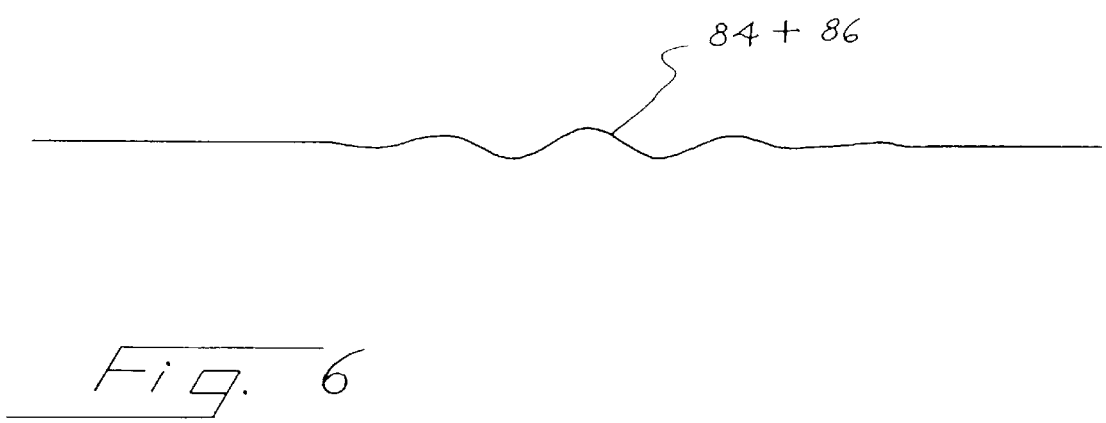

FIG. 5 can also be taken as a representation of the fundamental components 84, 86 of the receive beams R1, R2, respectively, assuming a different amplitude scale. The fundamental components 84, 86 of the receive beams are created by linear echoes of the fundamental components 80, 82 of the ultrasonic transmit beams, and the fundamental component 84 of the receive beam R1 is 180° out of phase with respect to the fundamental component 86 of the receive beam R2. FIG. 6 schematically shows the summation of the fundamental components 84, 86 of the receive beams R1, R2. Because the fundamental components 84, 86 are substantially equal in amplitude, and because they differ in phase by 180°, the fundamental components 84, 86 of the receive beams R1, R2 destructively interfere to a substantial extent.

Figure 7:
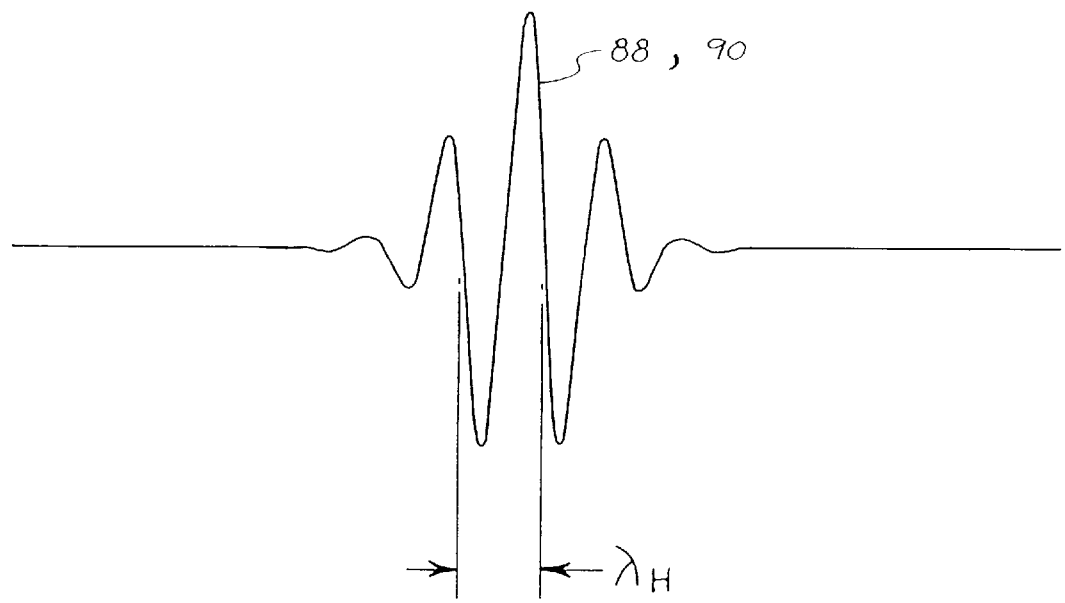
Figure 8:
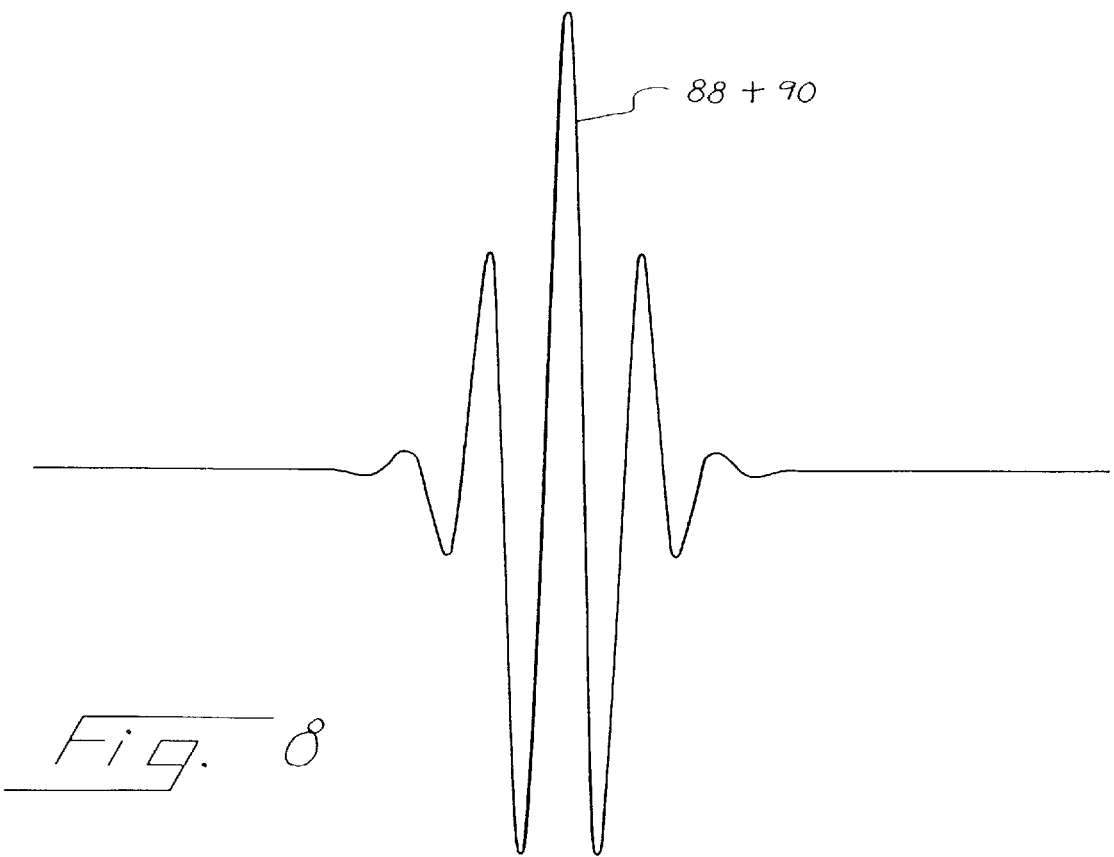

The situation is quite different with respect to the harmonic components of the receive beams R1, R2, as shown in FIG. 7. Because the harmonic components 88, 90 of the receive beams R1, R2 are created by non-linear effects, they are not characterized by a phase shift of 180°. In this case, the harmonic components 88, 90 are second harmonic components having a wavelength $\lambda_H$ equal to one-half of $\lambda_F$. In this case, the harmonic receive components 88, 90 have substantially the same phase, and when summed they constructively interfere as shown in FIG. 8.

In general, the fundamental components of the receive beams will not destructively interfere completely. Nevertheless, in this embodiment the fundamental components of the receive beams destructively interfere to a greater extent than the harmonic components of the receive beams, such that the harmonic components of the receive beams are emphasized in the composite signals.

Figure 10:
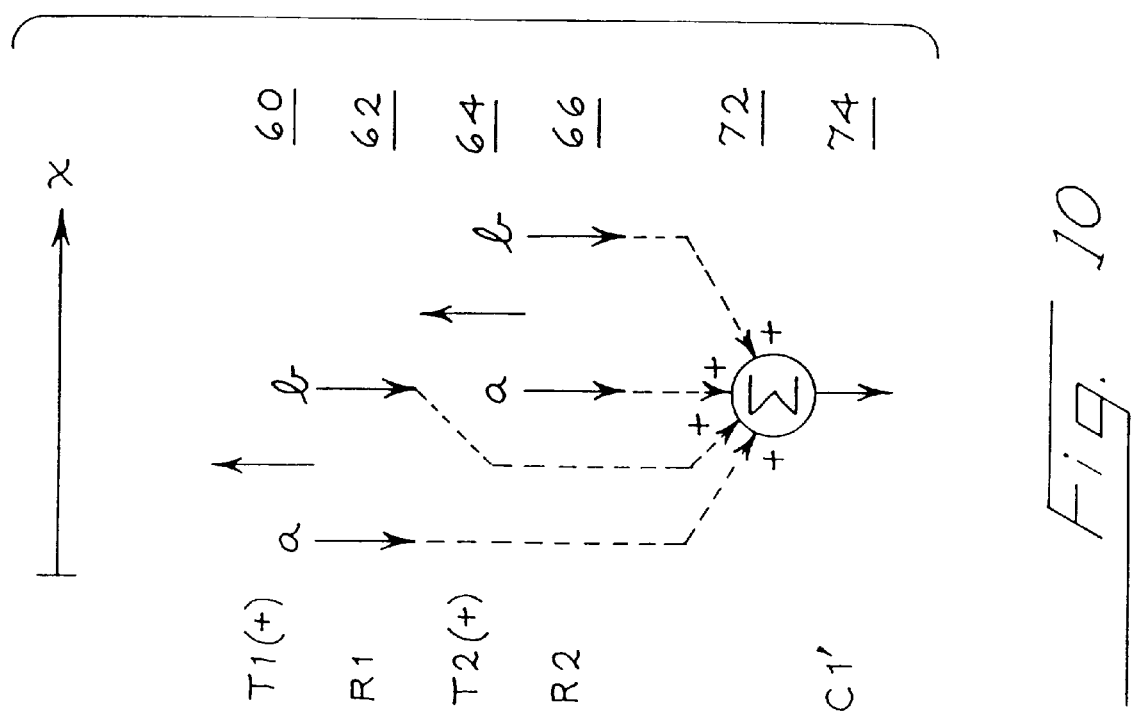
FIGS. 9 and 10 are schematic diagrams of alternative embodiments in which multiple receive beams are acquired for each transmit beam.
Figure 9:
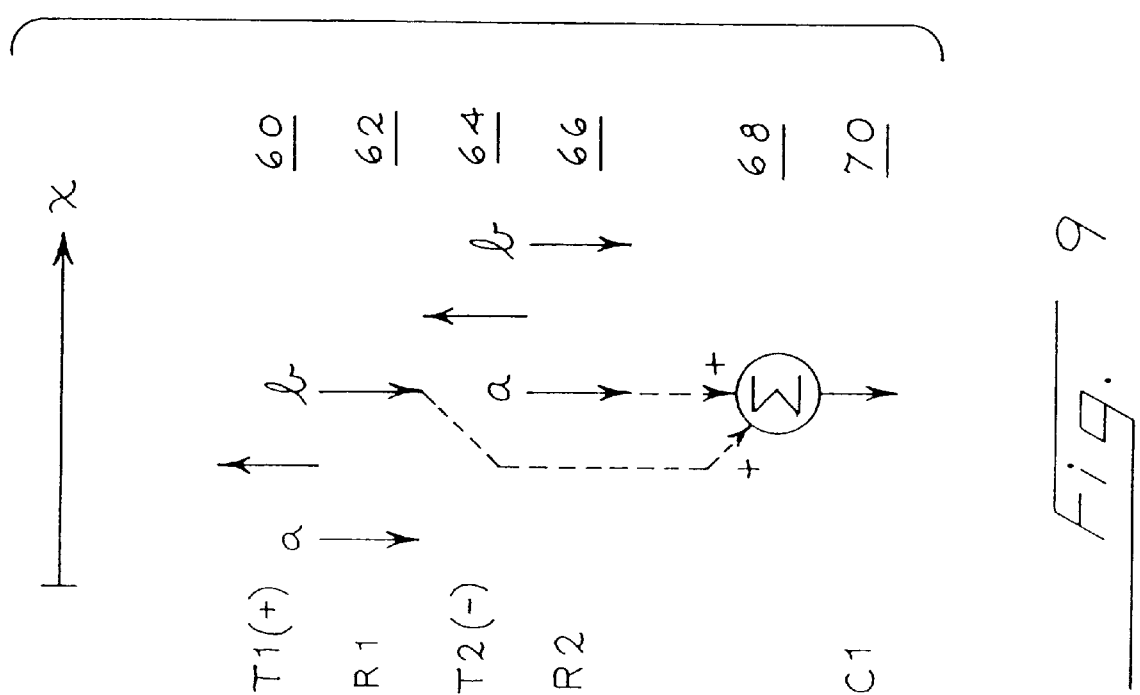

FIGS. 9 and 10 relate to multiple receive beam embodiments of this invention. In the method diagrammed in FIG. 9, a first transmit beam T1 (of positive polarity) is transmitted along a first azimuthal direction in step 60, and two associated receive beams R1a, R1b are acquired in step 62. Multiple-receive-beam beamformers are described in U.S. Pat. No. 5,827,188, assigned to the assignee of the present invention. Note that the receive beams R1a, R1b are offset spatially on respective sides of the transmit beam T1. In step 64, a second transmit beam T2 (of negative polarity) is transmitted along a second transmit direction, spatially distinct from the first transmit direction of the transmit beam T1. Two corresponding receive beams R2a, R2b are acquired in step 66, and two spatially aligned receive beams R1b, R2a are added together in step 68. Note that the summed receive beams R1b, R2a are spatially aligned along the azimuthal direction, but that they are associated with spatially distinct transmit beams T1, T2, respectively. The summing step 68 generates a composite signal C1 that is applied to the image processor in step 70. The method of FIG. 9 is anticipated to provide particularly good rejection of the fundamental component in the composite signal, due to the fact that the summed receive beams R1b and R2a are spatially aligned.

FIG. 10 shows a modified form of the method of FIG. 9, in which steps 60–66 are performed as described previously. In this case, the summing step 72 sums a total of four receive beams R1a, R1b, R2a, R2b to produce the composite signal C1' that is applied to the image processor in step 74.

In the methods shown in FIGS. 3, 4, 9 and 10, only a single composite signal is created. In practice, the illustrated methods are repeated as further transmit beams are fired and further receive beams are acquired.

Figure 12:
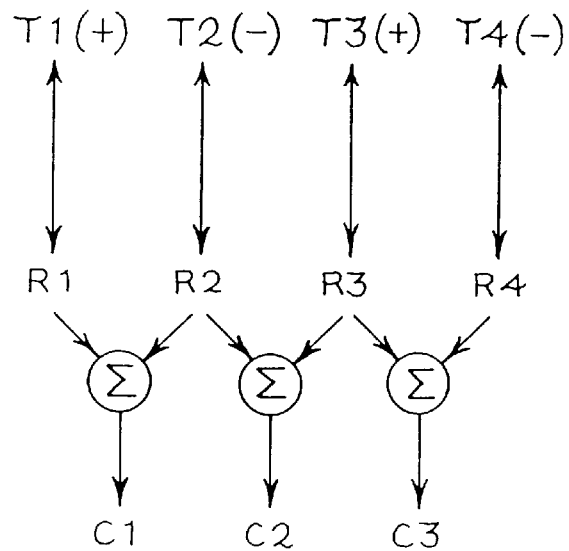
FIGS. 12 and 13 are schematic diagrams of the methods of FIGS. 3 and 9, respectively.
Figure 13:
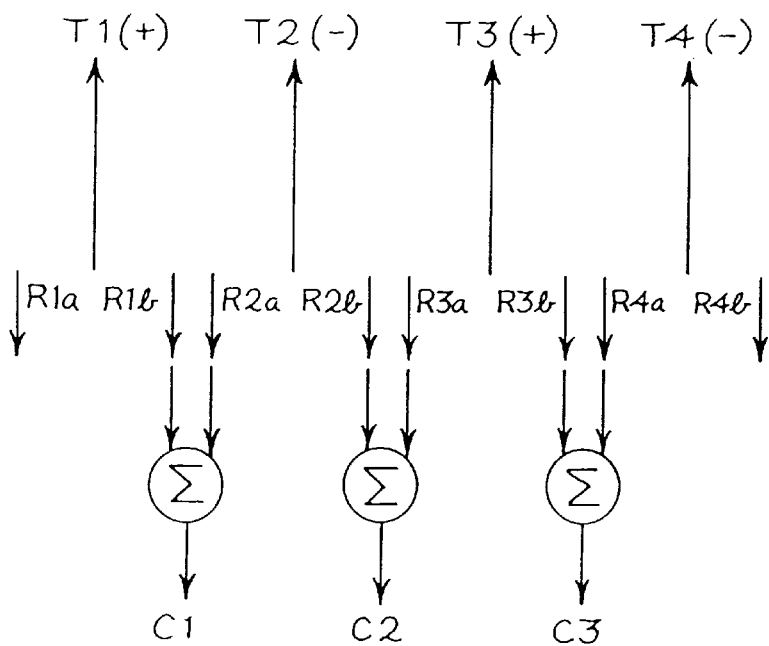

FIG. 12 shows the manner in which the method of FIG. 3 can be used with multiple transmit beams that traverse the region of interest. In FIG. 12, four transmit beams T1–T4 of alternating polarity are used to acquire associated receive beams R1–R4 that are summed as shown to produce composite signals C1–C3. Thus, three composite signals C1–C3 are acquired using only four transmit events. Similarly, FIG. 13 shows the manner in which the method of FIG. 9 can be used with transmit beams that traverse the region of interest. In these examples, the advantage of fundamental component rejection is obtained without any substantial penalty in frame rate, since the summed receive signals are associated with spatially distinct transmit beams.

In multiple receive beam embodiments such as those discussed above in conjunction with FIGS. 9 and 13, the receive beams associated with a single transmit beam may be combined to produce an intermediate combined beam aligned with the respective transmit beam. This intermediate combined beam does not provide cancellation of fundamental or harmonic components, but it may be useful in various frequency compounding techniques.

Figure 11:
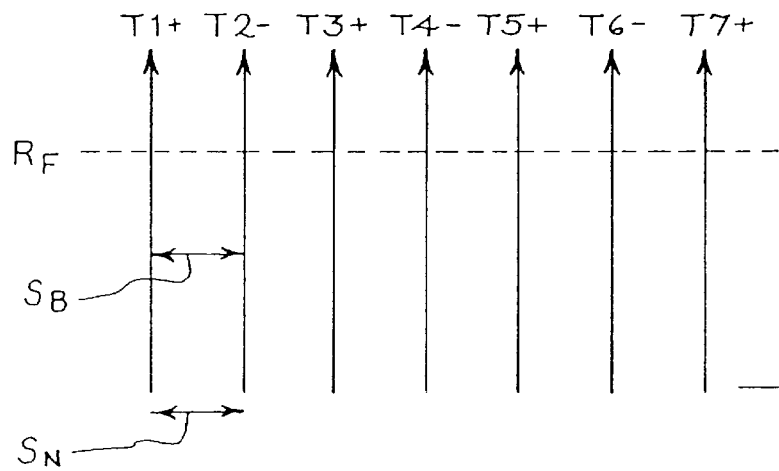
FIG. 11 is a diagram showing the spacing of a set of transmit beams generated by the system of FIG. 1 as compared to the Nyquist spacing.

FIG. 11 schematically shows an array of transmit beams T1–T7 that can be used in the methods described above. In FIG. 11, the focal range $R_F$ is illustrated, and the separation between adjacent transmit beams is indicated by the symbol $S_B$. In FIG. 11 the Nyquist spacing (i.e. the beam spacing required for Nyquist sampling) is shown by the symbol $S_N$. In this embodiment, there is a trade-off between azimuthal spacing of the transmit beams and selective enhancement of the harmonic component in the summing step described above. In particular, if the beam spacing $S_B$ is equal to the Nyquist spacing $S_N$, an associated azimuthal resolution and level of fundamental component suppression will be obtained. If the transmit beams are positioned more closely together such that the ratio $S_B/S_N$ is less than one, the level of fundamental suppression will be improved in the composite signals at the expense of increased time to acquire a frame of image data. Depending upon the degree of improvement desired in the level of fundamental suppression, the ratio $S_B/S_N$ can be made greater or less than one-half.

In another mode of operation, the ratio $S_B/S_N$ can be made greater than one such that the azimuthal dimension is sampled with a spacing greater than the Nyquist spacing $S_N$. In this case, the time required to acquire a frame is reduced, but the level of suppression of the fundamental component in the composite signal is reduced. Relationships between the beam spacing $S_B$ and the Nyquist spacing $S_N$ described above can be applied either at the focal range $R_F$ or ranges spaced from the focal range $R_F$.

For a given transmit line density there is substantially no adverse impact on frame rate due to the use of the fundamental suppression method described above. The fundamental components of the receive beams in general will not be perfectly cancelled due to the fact that the associated transmit beams are spatially distinct, and therefore the phase difference between the fundamental components of the summed receive beams will often be substantially different than 180° such as 180°±30° or 180°±45°. However, the more closely the transmit beams are spaced (the more over sampled they are) the better the fundamental cancellation in the composite signal that will be achieved. Thus, the method described above allows a trade-off between frame rate and degree of fundamental rejection in the composite signal. The positive and negative polarity ultrasound lines can approach each other by increasing line density and thereby increasing the rejection of the fundamental component in the composite signal. As a greater degree of over-sampling is used, degradation of lateral resolution associated with the summing step is also reduced.

The alternating line phase embodiments described above alternate the polarity of the phase of the transmit beam across scan lines. Coherent combination of the pre-detection receive beams cancels fundamental signals and enhances second harmonic signals, thereby allowing an increase in axial resolution. This technique offers a tradeoff between additional rejection of the fundamental component and frame rate as a function of the selected line density. When operated at Nyquist line spacing, the alternating line phase technique described above can provide additional rejection at up to two times the frame rate of conventional two-pulse techniques.

The alternating line phase techniques can be used (1) to create combined beams that cancel fundamental components and enhance even harmonic components, as described above (by adding the respective receive beams), or (2) to create combined beams that cancel even harmonic components and enhance fundamental components (by subtracting the respective receive beams). If desired, two different combined beams may be generated from a single set of receive beams, one combined beam emphasizing even harmonic components and the other combined beam emphasizing odd harmonic components. Such combined beams can be compounded to reduce speckle effects.

The combined signals described above with enhanced second harmonic components and cancelled or suppressed fundamental components may be used in any of the aberration correction techniques described in U.S. patent application Ser. No. 09/061,082 filed Apr. 15, 1998, assigned to the assignee of this invention and hereby incorporated by reference.

As described above, receive signals Y1, Y2 associated with differently-phased transmit beams T1, T2 may be combined by addition (to emphasize the even harmonic components) or by subtraction (to emphasize the fundamental components). Other combinations of Y1 and Y2 are possible, as described for example in Bradley U.S. patent application Ser. No. 60/095,768, filed Aug. 7, 1998, assigned to the assignee of this invention and hereby incorporated by reference in its entirety. As described in this patent application, the combined signal Zn can take the form $$Zn=|Y1|^n-|Y2|^n$$

where n is a small positive integer. $Z_1$ corresponds to the first harmonic component; $Z_2$ corresponds to a compounded combination of the fundamental and first harmonic components. As used herein, the term "combining" is intended broadly to encompass both linear and nonlinear combinations, including the examples set out above as well as other useful combinations of receive signals or beams.

Simply by way of example, the alternating line phase techniques described above can be implemented using a Sequoia™ ultrasonic imaging system available from Acuson Corporation, Mountain View, Calif., using an Acuson 8L5 transducer. By way of example, the Sequoia™ imaging system can be programmed with the following scan parameters.

transmit f number—1.85
transmit apodization—half circle
receive f number—1.00
receive apodization—uniform
transmit center frequency—3.5 MHz
receive center frequency—7.0 MHz
transmit focus—25 mm
receive focus—10–25 mm Of course, all of these parameters can readily be modified as desired, depending on the application. Multiple simultaneous transmit beam techniques can be used if desired.

Alternating Line Aperture Embodiments

In the alternating line aperture embodiments of this invention, the transmit aperture, the receive aperture, or both can be alternated across scan lines. Coherent combination of at least two of the pre-detection receive beams forms a synthetic aperture sum which may increase lateral resolution. In alternative embodiments, the alternate apertures may be left/right, inside/outside, even/odd elements of the transducer, or other variations. For example, transmit beams T1–T4 and receive beams R1–R4 can be created in the geometry shown in FIG. 12 discussed above. Adjacent receive beams R1–R2, R2–R3, R3–R4 can be combined to produce composite beams C1, C2 and C3. The system 10 of FIG. 1 can be used to implement these alternating line embodiments. For these embodiments the transmit beams T1–T4 can be all of the same polarity, rather than of alternating polarity as described above in conjunction with FIG. 12.

As shown in FIG. 14, the transmit beams can be provided with a transmit aperture 100 that is centered on the origin 102 of the respective transmit beam. As the origins 102 shift laterally for successive transmit beams, the transmit apertures 100 are shifted in a similar manner.

In this embodiment the receive beams can be considered to be of two types which alternate across the region being imaged. These two types differ in receive aperture. For example, as shown in FIG. 15, receive beams of the first type (R1, R3, . . . ) are acquired with a receive aperture 104 at the left side of the transducer, and receive beams of the second type (R2, R4, . . . ) are acquired with a receive aperture 106 at the right side of the transducer. If desired, the left and right receive apertures 104, 106 may translate across the face of the transducer to follow the origin of the respective receive beams, as shown in FIG. 16. FIG. 16 shows one of the receive apertures wrapping from right to left in receive line R2, though such wrapping is not required.

Figure 17:
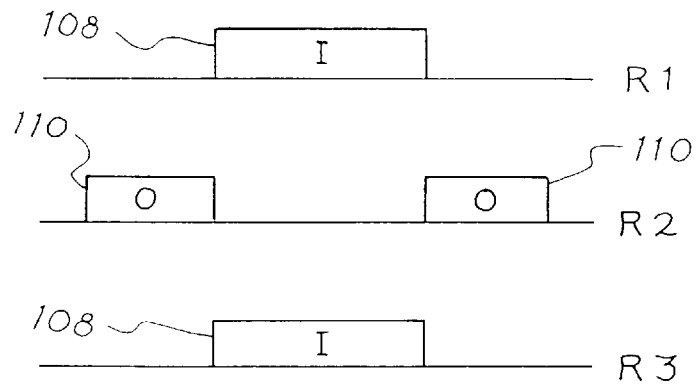
Figure 18:
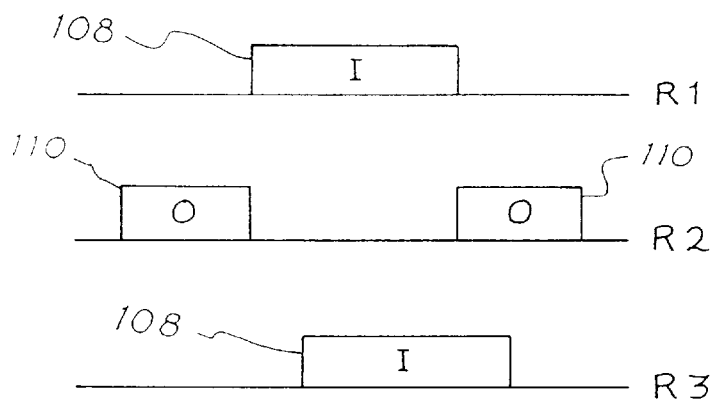
Figure 19:

FIG. 17 and 18 relate to alternative embodiments in which the receive aperture is divided into an inside portion 108 and two outside portions 110. The receive beams of the first type are acquired using the inside receive aperture 108, and receive beams of the second type are acquired using the outside receive aperture 110. As shown in FIG. 18, the inside and outside receive apertures 108, 110 can be moved across the face of the transducer so as to remain centered on the origin of the respective receive lines, with or without wrapping.

Many other apertures may be used for the two or more receive apertures associated with respective receive beams. For example, as shown in FIG. 24, even transducer elements may be used for a first receive aperture 108 for receive beams of the first type, and odd transducer elements may be used for a second receive aperture 110 for receive beams of the second type.

With this arrangement the receive beams that are combined to create the composite beams are of differing types, and the combined beams are therefore characterized by a synthetic aperture that includes signal information associated with multiple apertures (e.g., left/right, inside/outside, or even/odd) in the various embodiments discussed above.

By way of example, the Acuson Sequoia™ ultrasonic imaging system can be used with an Acuson 8L5 transducer to implement the alternating line aperture embodiments described above. By way of example, the following scan parameters can be used:

transmit f number—2.0
transmit apodization—half circle
receive f number—1.0
receive apodization—uniform transmit focus—25 mm receive focus—10–25 mm As before, all of these parameters can readily be modified as desired, depending on the application.

Though not shown in the drawings, a multiple receive beam acquisition method similar to that of FIG. 13 can also be modified to provide the alternating line aperture features discussed above.

If desired, the transmit aperture may also be varied between the first and second types of receive beams, and in some cases more than two types of beams will be appropriate. For example, three different receive apertures can be provided, and three receive beams (one from each aperture type) can be coherently summed to create a synthetic aperture combined beam.

Alternating Line Focus Embodiments

In these embodiments the location of the transmit focus is alternated across scan lines. Coherent combination of the associated receive beams forms a composite beam with improved transmit depth of field at higher frame rates as compared to standard sequential focusing methods, in which multiple segmented portions of an image are acquired with separate respective transmit beams are stitched together.

Figure 20:
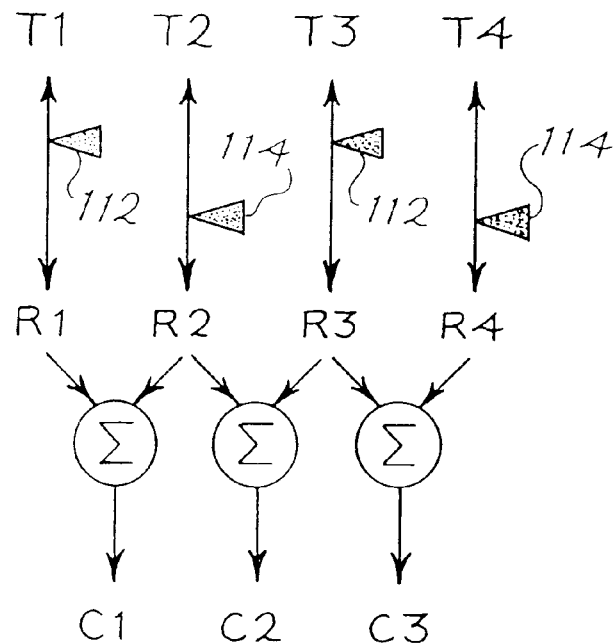
FIG. 20 is a flowchart showing an alternating line focus embodiment of this invention.

By way of example, FIG. 20 shows a schematic view of a beam acquisition method similar to that of FIG. 12. In the schematic view of FIG. 20, the transmit focus 112, 114 is indicated by a dark triangle. As shown in FIG. 20, transmit beams of the first type (T1, T3, . . . ) are characterized by a relatively deep transmit focus 112, and transmit beams of the second type (T2, T4, . . . ) are characterized by a relatively shallow transmit focus 114. Receive beams R1–R2, R2–R3, R3–R4, . . . are combined, and in each case the combined receive beams are associated with transmit beams of the first type as well as transmit beams of the second type. Thus, the resulting composite beams C1, C2, C3 . . . have an improved transmit depth of field.

Though not shown in the drawings, a multiple receive beam acquisition method similar to that of FIG. 13 can also readily be modified to provide the alternating line focus features discussed above.

Alternating Line Frequency Embodiments

At any given system operating frequency (system sampling rate, filter bandwidth, and so forth), there exists only a limited amount of pulse bandwidth, which can be less than that available from the transducer.

In the alternating line frequency embodiments of this invention, the receive beamformer frequency of operation (system sampling rates, filter bandwidths, and so forth) are alternated from scan line to scan line. Coherent combination of these lines forms a composite line with increased bandwidth at higher frame rates as compared with conventional multipulse methods.

Figure 21:
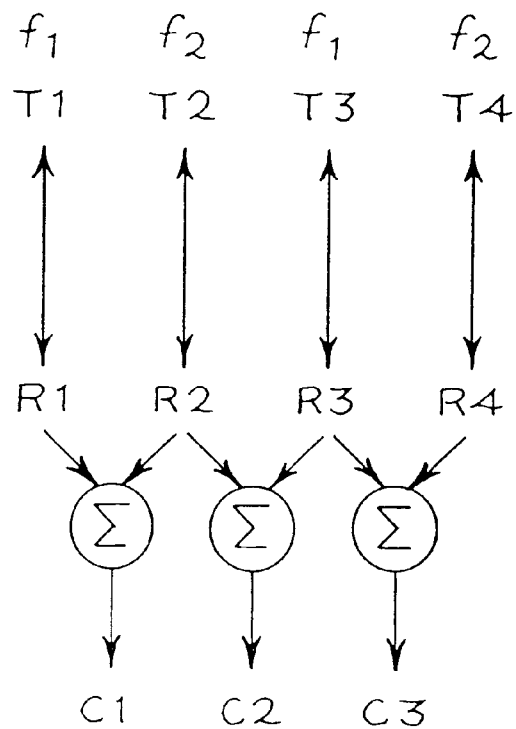
FIG. 21 is a flowchart showing an alternating line frequency embodiment of this invention.
Figure 22:
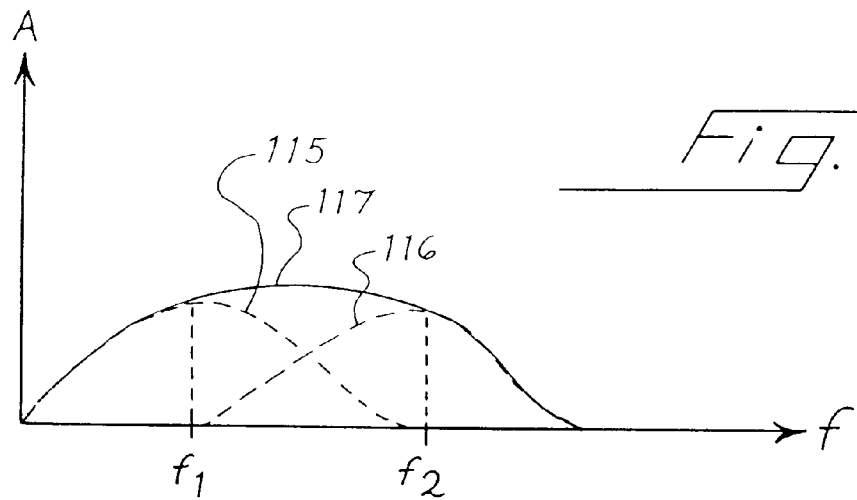
FIG. 22 is a graph showing frequency characteristics of the embodiment of FIG. 21.

FIG. 21 shows an embodiment of this invention in which the receive lines of the first type (R1, R3, . . . ) are acquired with a frequency of operation f1, while receive beams of a second type (R2, R4, . . . ) are acquired with a frequency of operation f2. Adjacent receive beams of the first and second type are coherently combined to produce composite beams C1, C2, C3, having an increased bandwidth, as shown in FIG. 22. In FIG. 22, the bandwidth of the receive beams of the first and second types are shown at 115, 116, respectively, and the bandwidth of the composite beams is shown at 117. This advantage of a large bandwidth for the composite beams is obtained at a high frame rate.

Though not shown in the drawings, the alternating line frequency embodiments can also implement a multiple receive beam acquisition scheme similar to that of FIG. 13, in which multiple receive beams are acquired in response to each respective transmit beam.

Alternating Line Complex Phase Angle Embodiments

Copending U.S. patent application Ser. No. 09/282,799 which is hereby incorporated by reference in its entirety, discloses ultrasound imaging methods and systems that combine receive signals from at least two separate transmit pulses that are created from respective components of a desired complex insonification signal that differ in the complex phase angle.

For example, each transmit pulse $h_R(t)$ can be expressed as follows:

$$h_k(t)=Re\{a(t)exp\{j2\pi f_c t+j\theta_k\}\}$$

In this representation, the term $(j\theta_k)$ is the complex phase angle of the transmit pulse $h_k(t)$, and the transmit pulses $h_k(t)$ are examples of respective components of a single complex insonification signal that differ in complex phase angle. As explained in detail in above-identified application Ser. No. 09/282,799, the complex phase angles can be selected such that the combined echo signals associated with the transmit pulses exhibit one or more of the following features: selective enhancement of harmonic components of the echo signals, selective enhancement of fundamental components of the echo signals, selective cancellation of unwanted frequency spectra to lower the overall frequency bandwidth and thereby to reduce the sampling rate requirement. The echo signals can be combined in a coherent manner prior to detection, or alternately can be combined subsequent to detection.

One example of this alternating line mode is shown in FIG. 24, in which the complex phase angle ok for scan line k is equal to $\theta_1$ for even scan lines (k=2,4, . . . ) and $\theta_2$ for odd scan lines (k=1,3, . . . ).

The difference between $\theta_1$ and $\theta_2$ can be selected as appropriate for the application. For example, the difference can be about 90° in one embodiment.

As shown in FIG. 24, transmit lines T1, T2 and T3 are successively fired along respective scan lines 1, 2 and 3 in steps 170, 174 and 178, respectively. Receive beams R1, R2, and R3 are acquired in steps 172, 176 and 180, respectively. Each of the receive beams R1, R2, R3 is spatially aligned with the respective transmit beam T1, T2, T3. The transmit beams T1, T2, T3 differ in complex phase angle, with transmit beams T1 and T3 having the complex phase angle $\theta_1$ and the transmit beam T2 having the complex angle $\theta_2$. In step 182, the receive beams R1 and R2 are combined to generate respective composite signals C1 and C2. In step 184, the composite signals C1 and C2 are applied to an image processor for further processing.

Though not shown in the drawings, the alternating complex phase angle embodiments can also implement a multiple receive beam acquisition scheme similar that to FIG. 13, in which multiple receive beams are required in response to each respective transmit beam. Also, multiple simultaneous transmit beams can be used.

This mode is one example of the general class of alternating line modes in which the transmit waveform is alternated from scan line to scan line. There are many other examples, including the alternating line transmit code embodiments described below. Also, other characteristics of the transmit waveform can be alternated, including transmit center frequency, bandwidth, spectral shape, and presence/absence of selected components such as a fractional-harmonic seed. See the discussion of fractional harmonic seeds and several multi-pulse methods as described in copending U.S. patent application Ser. No. 09/282,603, now U.S. Pat. No. 6,117,082, for further details. The entirety of this application is hereby incorporated by reference herein.

Alternating Line Transmit Gain Embodiments

In these embodiments of the invention, the transmit power or gain is alternated from scan line to scan line. For example, transmit beams T1, T3, T5 . . . on odd scan lines can be fired with a low transmit gain and transmit beams T2, T4, T6 . . . on even scan lines can be fired with high transmit gain. The resulting echo signals can then be combined with weighting factors selected to cause the composite signals to selectively enhance either harmonic or fundamental components of the echo signals.

Figure 26:
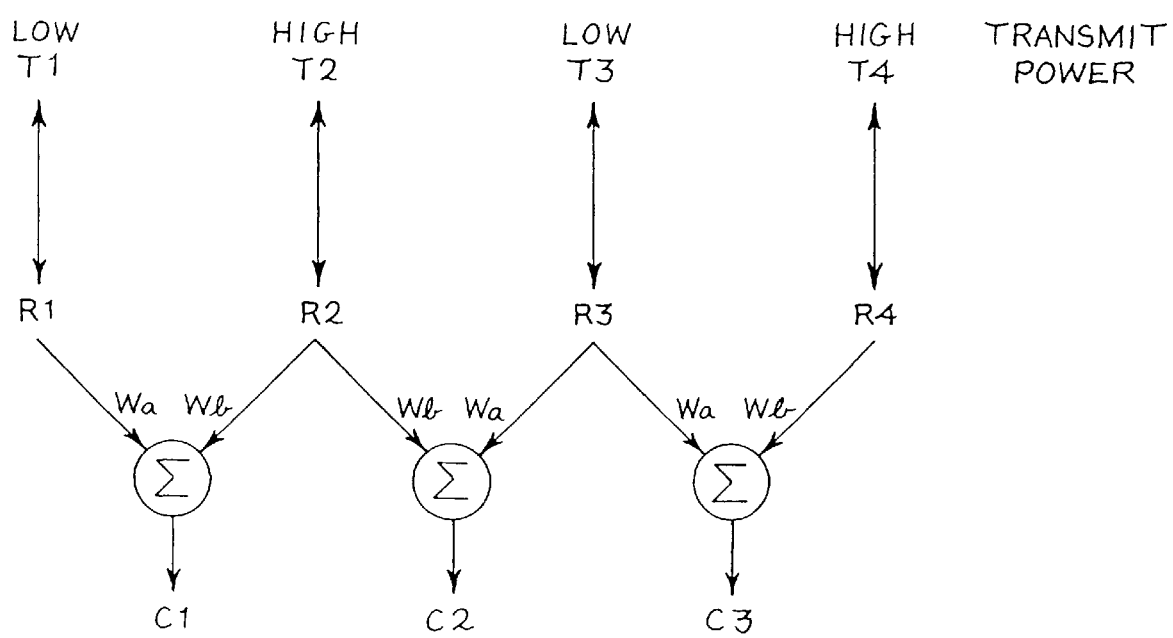
FIG. 26 is a schematic diagram of the embodiment of FIG. 25.

One specific embodiment is flowcharted in FIG. 25 and schematically illustrated in FIG. 26. In step 190, a first transmit beam is transmitted with low transmit power, and in step 192 one or more receive beams are received and stored. In step 194, a second transmit beam is transmitted with high transmit power, and in step 196 one or more second receive beams are received and stored. In step 198, selected first and second receive beams are weighted and combined to form composite signals which are supplied to an image processor in step 200. Note in FIG. 26 that in this embodiment the receive signals R1, R3, . . . associated with lower power transmit signals are weighted with a weighting factor $W_A$, while the receive signals R2, R4 . . . associated with high power transmission signals are weighted with a weighting factor $W_B$.

Figures 27, 29:
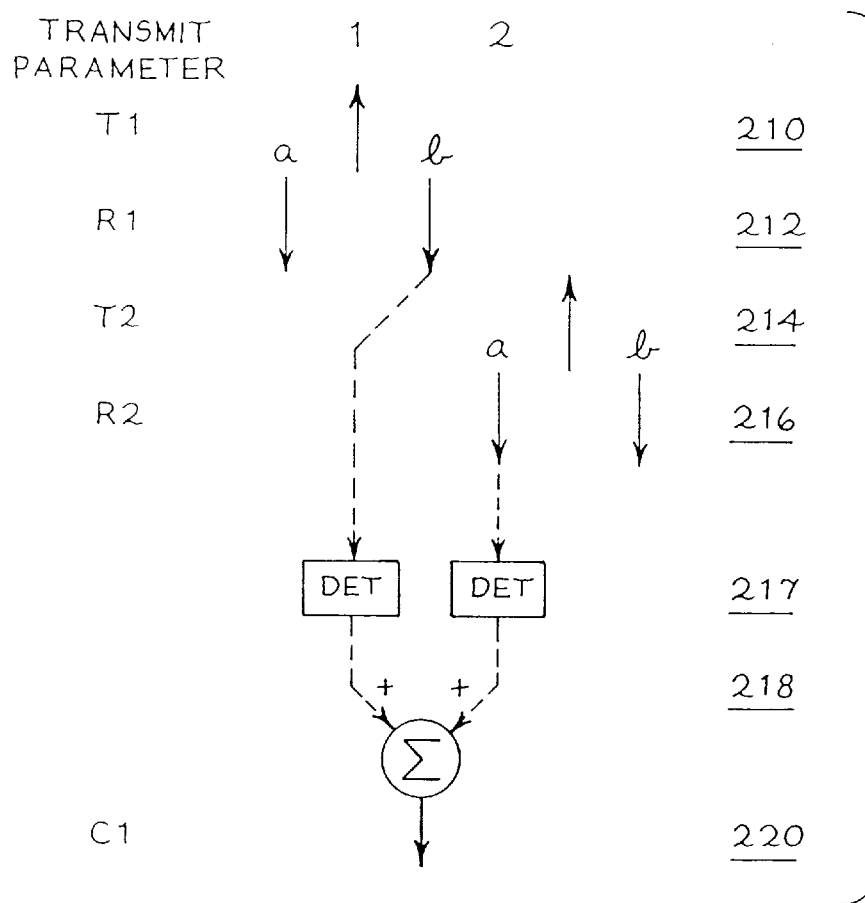
FIG. 27 is a chart illustrating alternative modes of operation of the embodiment of FIG. 26.
FIG. 29 is a schematic diagram illustrating the embodiment of FIG. 28.

FIG. 27 illustrates one embodiment of the general method of FIGS. 25 and 26. In the example of FIG. 27, odd numbered scan lines use a transmit gain of 1 and even numbered scan lines use a transmit gain of 2. In this example, the composite signals C1, C2, . . . emphasize the second harmonic component of the echo signals when $W_A$ is set equal to 2 and $W_B$ is set equal to -1. Alternatively, the composite signals C1, C2, . . . emphasize the fundamental component of the echo signals when $W_A$ is set equal to 4 and $W_B$ is set equal to -1. This is because the amplitude of the fundamental components of the echo signals scale substantially linearly with transmit gain, while the amplitudes of the second harmonic components of the echo signals scale approximately with the square of the transmit gain. The combining step 198 of FIG. 25 is preferably performed following detection, though it can be placed at other points along the processing path.

As before, these embodiments can also use multiple simultaneous transmit beam techniques and multiple simultaneous receive beam techniques.

Alternating Line Compounding Embodiments

Another alternating line mode applies the techniques discussed above to achieve speckle reduction. In the embodiment shown in FIGS. 28 and 29, spaced transmit firings are used and multiple receive beams are formed from each transmit firing. Two or more receive beams from each transmit beam are compounded to form composite signals that receive contributions from two or more spatially distinct transmit beams. In this way, image quality is improved.

Figure 28:
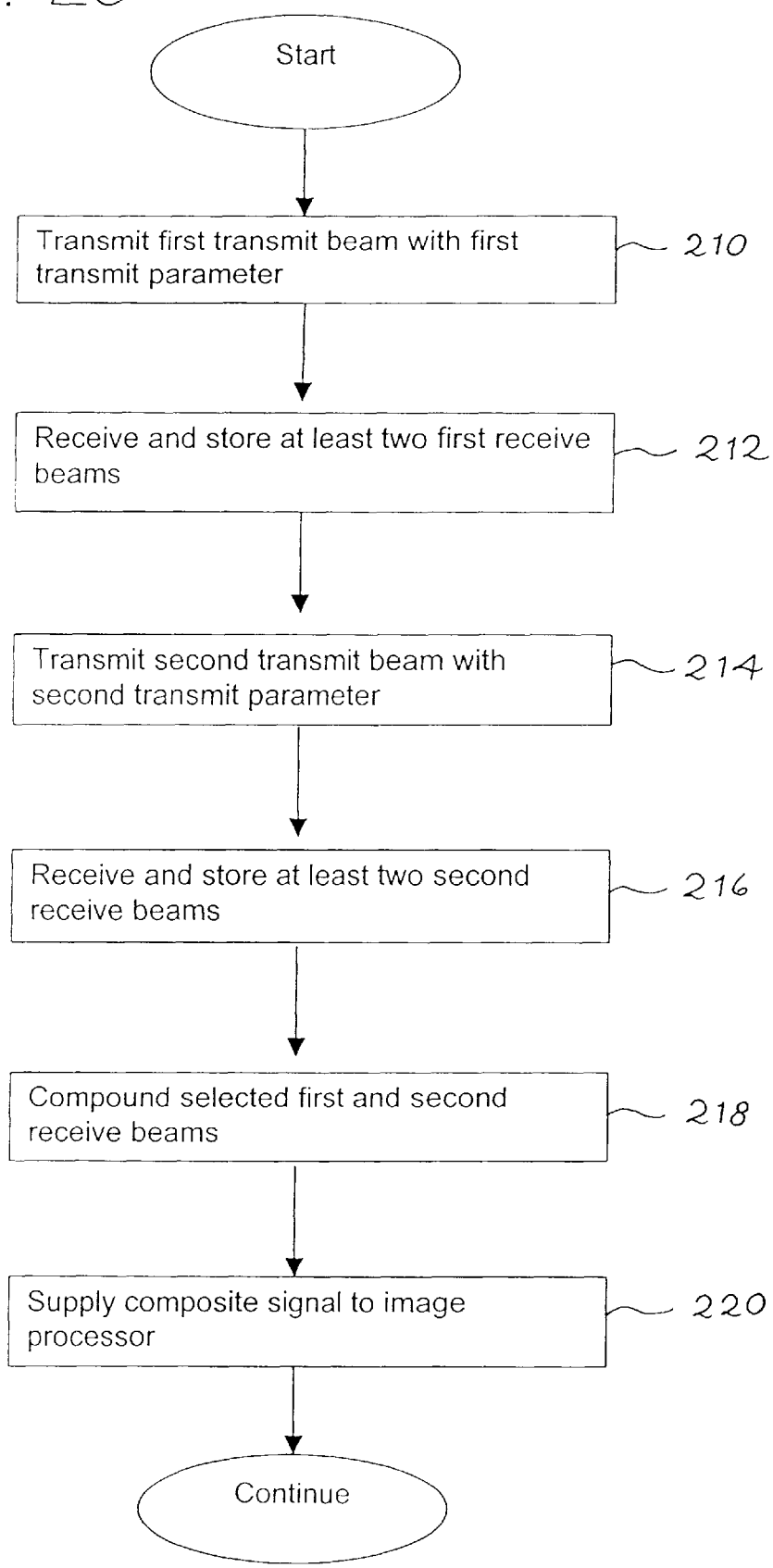
FIG. 28 is a flowchart showing an alternating line compounding embodiment of this invention.

As shown in the example of FIG. 28, one ultrasonic imaging method of this type includes steps 210 through 220. The method is schematically shown in FIG. 29. In step 200, a first transmit beam is fired along a first scan line direction and, in step 212, two receive beams R1a, R1b are received. The receive beams R1a and R1b in this embodiment are spaced on respective sides of the transmit beam T1. In step 214, a second transmit beam T2 is fired along a second transmit line, spaced from the first, and in step 216 two receive beams R2a and R2b are received on respective sides of the transmit beam T2. The transmit beams T1, T2 differ in any desired transmit scan parameter, including any of the parameters described in the various alternating line methods described in this specification. In this embodiment, the receive beams R1b and R2a are spatially aligned with one another and spatially distinct from the transmit beams T1, T2. In step 217, the receive beams R1a and R2b are detected, and in step 218, the receive beams R1b and R2a are compounded (subsequent to detection) to generate a composite signal C1 that is supplied to the image processor in step 220.

The method of FIGS. 28 and 28 can be modified. For example, three, four or more receive beams can be acquired in response to each transmit beam. If desired, an axicon transmit beam focus can be used. In order to improve speckle reduction, the transmit beams T1 and T2 associated with a single composite signal or the receive beams R1b, R2a associated with a combined signal can differ from one another in many ways to enhance speckle reduction. For example, any of the following parameters can be alternated between transmit beams and/or receive beams: transmit focus transmit/receive center frequency, transmit gain, transmit aperture/apodization, receive gain, receive aperture/apodization, receive filter (high/low/wide/narrow), axicon transmit/circular receive, axicon receive/circular transmit. If desired, delays used for beamforming may be selected to degrade spatial resolution.

In elevation compounding, when two two-dimensional frames that differ in elevation angle are combined, the compounded two-dimensional frames may differ in any of a number of parameters to enhance speckle reduction, including the following: beam origins, apodization profiles, multiple/single receive beam per transmit event, multiple transmit foci (simultaneous or sequential), different transmit focal depths, or dynamic transmit focusing as described in Hossack U.S. Pat. No. 5,608,690.

Alternating Line Polarity Sequence Embodiments

The embodiments described above have involved firing only a single transmit beam along each scan direction. These embodiments can be considered examples of the invention in which the set of transmit beams in each scan direction is equal to 1. Other embodiments of this invention include more than one transmit beam within each set of transmit lines steered to a specific scan line. For example, the polarity sequence can be alternated from transmit scan line to transmit scan line as described below.

Figures 31, 32:
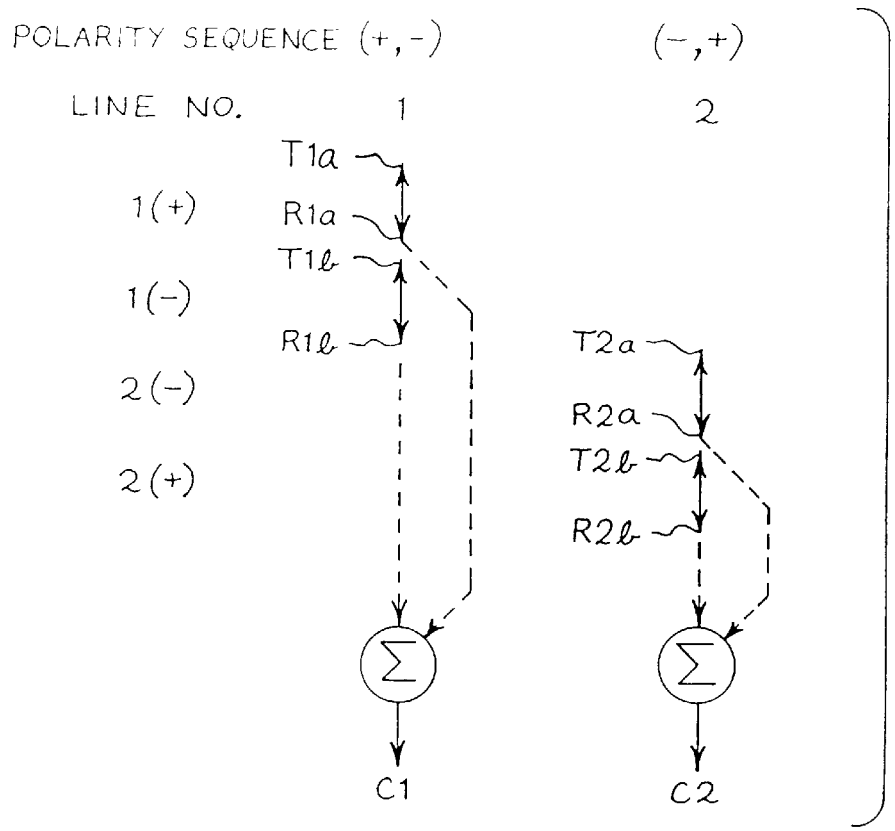
FIG. 31 is a schematic diagram illustrating operation of the embodiment of FIG. 30.
FIG. 32 is a schematic diagram illustrating operation of another embodiment of an alternating line polarity sequence embodiment of this invention.

FIG. 31 shows a schematic representation of one embodiment of an alternating line polarity sequence embodiment. In this embodiment transmit line T1 a is fired along a first scan line and an associated receive line R1a is then acquired. Then a second transmit beam T1b is fired along the same scan line and the corresponding receive signal R1b is acquired. In this embodiment, the transmit beams T1a and T1b are identical in waveform but opposite in polarity. Receive beams R1a and R1b are combined in a coherent summing operation prior to detection to generate the first combined signal C1. These steps are included in the step 230 of the flowchart of FIG. 30.

Transmit beams T2a (-polarity) and T2b (+polarity) are fired along a second scan line and associated receive beams R2a, R2b are acquired and coherently summed prior to detection to form a second combined signal C2 (step 232 of FIG. 30). The combined signals C1, C2 preferentially enhance even harmonic responses in the receive signals while suppressing fundamental and odd harmonic responses in view of the phase inversion of the two transmit beams on each transmit line.

From the foregoing description, it should be apparent that the transmit beams contributing to the combined signal C1 are fired with a first polarity sequence (+−) while the transmit beams associated with the second combined signal C2 are fired with a second, different polarity sequence (−+). In this example, the first polarity sequence (−+) is used for odd numbered scan lines, and the second polarity sequence (−+) is used for even numbered scan lines across the frame.

As shown in FIG. 32, this technique can also be used in two-dimensional imaging. In one example, the polarity sequence that is used for scan lines distributed in both the azimuthal and elevational direction can be arranged in a checkerboard fashion, as shown in FIG. 32. In this way, the polarity sequence alternates in both the elevation direction and the azimuthal direction.

Figure 34:
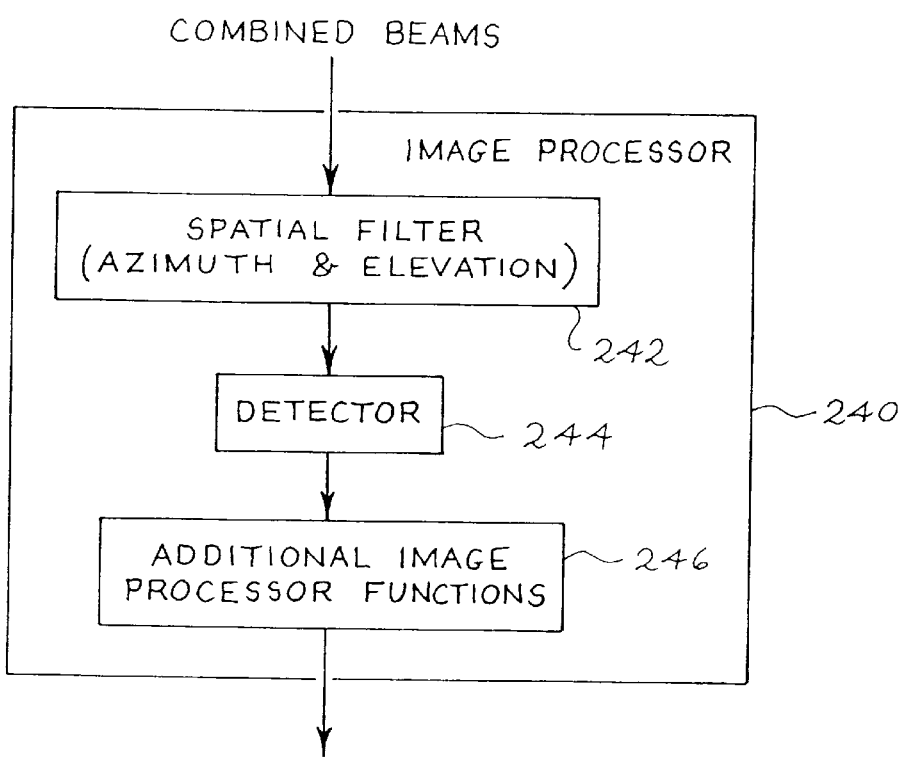
FIG. 34 is a block diagram of an image processor suitable for use in the embodiment of FIG. 1.

The combined signals C1, C2 or FIGS. 30 and 31 are preferably spatially filtered prior to detection as described in detail below in conjunction with FIG. 34. The combination of the alternating line techniques described above in conjunction with the pre-detection spatial filtering techniques described below enhance the suppression of undesired frequency components in the combined signal.

Alternative embodiments can use multiple transmit beam and/or multiple receive beam techniques. Also, more than two receive beams may be combined, and subtraction can be used instead of addition to form combined signals that emphasize the fundamental components.

Alternating Line Transmit Code Embodiments

As described in co-pending U.S. patent application Ser. No. 09/283,346, filed on the same date as the present application, multiple transmit codes can be used on successive transmit events. Related co-pending U.S. patent application Ser. No. 09/282,510 provides further information on coded transmit beams. The entirety of these two co-pending U.S. patent applications are hereby incorporated by reference for their teaching of such transmission codes. As explained in greater detail in this application, such transmit codes include transmit phase modulation codes and transmit amplitude modulation codes.

By varying the transmission code from transmit event to transmit event, the shape of the transmit pulse can be changed in such a way that the echo signals from transmit events with differing transmit codes have markedly different range lobes. By coherently combining echo signals having differing range lobes, undesired range lobes can be reduced or cancelled to a large extent. Examples of suitable codes that can be varied from transmit event to transmit event include frequency modulated codes and Golay codes. Frequency modulated codes include a wide variety of transmit pulses in which the zero crossings are unevenly spaced. Chirp pulses (of either the rising frequency or falling frequency type) are two examples.

Figure 33:
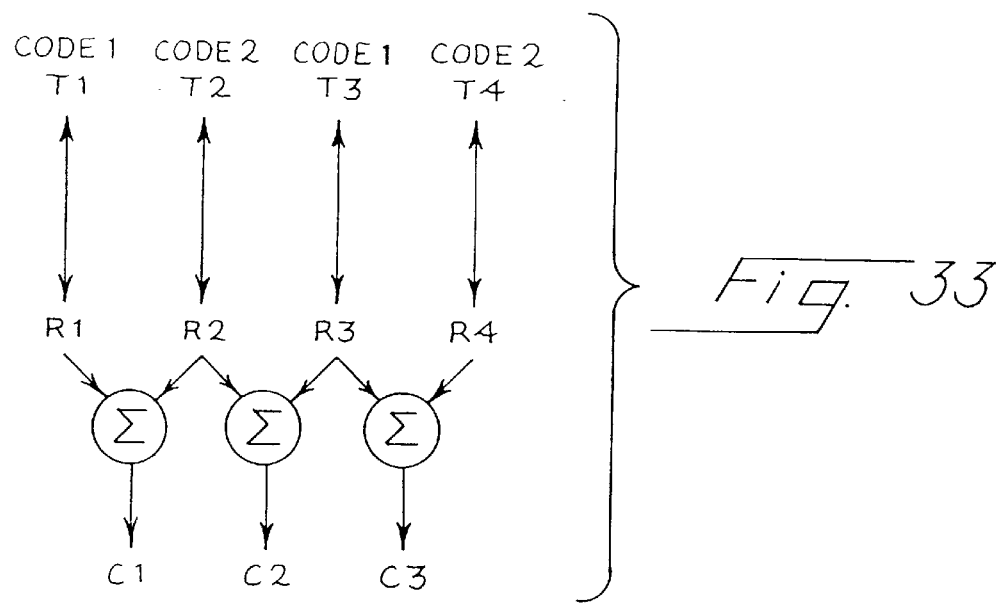
FIG. 33 is a schematic diagram of an alternating line transmit code embodiment of this invention.

FIG. 33 shows an embodiment of this invention in which transmit code I is used for transmit beams T1, T3 . . . on odd transmit lines and transmit code 2 is used for transmit beams T2, T4, . . . on even transmit lines. In this embodiment each transmit event produces a single transmit beam aligned with the respective scan line, and a single receive beam R1, R2, . . . is acquired from each respective transmit beam T1, T2 . . . . As shown in FIG. 33, consecutive receive beams associated with consecutive transmit beams of differing transmit code are coherently combined in a summing operation to produce composite signals C1, C2 . . . . By choosing the transmit codes such that the receive beams R1, R2 exhibit substantially different range lobes, such range lobes are suppressed in the combined signals C1, C2 . . . by virtue of the summing operation.

Though not shown in the drawings, alternating line transmit code embodiments can also implement a multiple receive beam acquisition scheme similar to that of FIG. 13, in which multiple receive beams are acquired in response to each respective transmit beam. Similarly, multiple simultaneous transmit beam techniques can be used with these embodiments.

Embodiments Employing Pre-Detection Spatial Filtering

In many embodiments, it is preferred to include a spatial filter prior to the detection operation in the image processor 32 of FIG. 1. FIG. 34 shows a diagram of a preferred image processor 240 that includes a spatial filter 242 positioned in the signal path upstream of the detector 244. Block 246 is used to indicate additional image processing functions, which can include any suitable functions, including conventional functions well-known to those skilled in the art.

The spatial filter 242 preferably performs an azimuthal and/or elevation pre-detection spatial filtering, and can include a real or complex filter. In one embodiment, the spatial filter 242 is made up of a combination of separable range, azimuthal, and elevation filters, which can use either constant filter coefficients or filter coefficients that are varied as a function of range and/or line (azimuth and/or elevation). In another alternative, the spatial filter 242 can include a non-separable spatial filter such as any of the following filters: range/azimuth, range/elevation, azimuth/elevation, or range/azimuth/elevation. As before, the filters may use constant filter coefficients or filter coefficients that vary as a function of range and/or line (azimuth and/or elevation). Preferably, the filters are low-pass filters that have a cutoff frequency determined by simulation or empirically for the particular application.

The combined beams that are applied to the spatial filter 242 can include any of the combined beams described above. For example, the combined beams may include the combined beams discussed above in conjunction with FIGS. 9 and 13, wherein the combined beams are formed from multiple receive beams associated with a single transmit beam. As another example, the combined beams can also include conventional pulse inversion receive beams such as those described in Chapman, U.S. Pat. No. 5,632,277. In these embodiments, the combined beams are formed as a combination of spatially aligned receive beams associated with spatially aligned transmit beams of opposite polarity.

Additional Embodiments

Other embodiments of this invention transmit a set of ultrasonic transmit beams into a region, including in some cases spatially aligned transmit beams.

Fundamental components of selected transmit beams are characterized by a phase difference of 180°. Ultrasonic receive beams are acquired from the region, and multiple receive beams are associated with each respective one of the transmit beams. At least two receive beams are summed to form a composite signal, and the phase difference in the fundamental transmit components is effective to cause fundamental components of the receive beams to destructively interfere to a greater extent than harmonic components of the receive beams. In some embodiments, three or more receive beams are summed to form the composite signal.

For example, the system of FIG. 1 can be used to practice the methods of FIGS. 9 and 10 with spatially aligned transmit beams.

Figure 23:
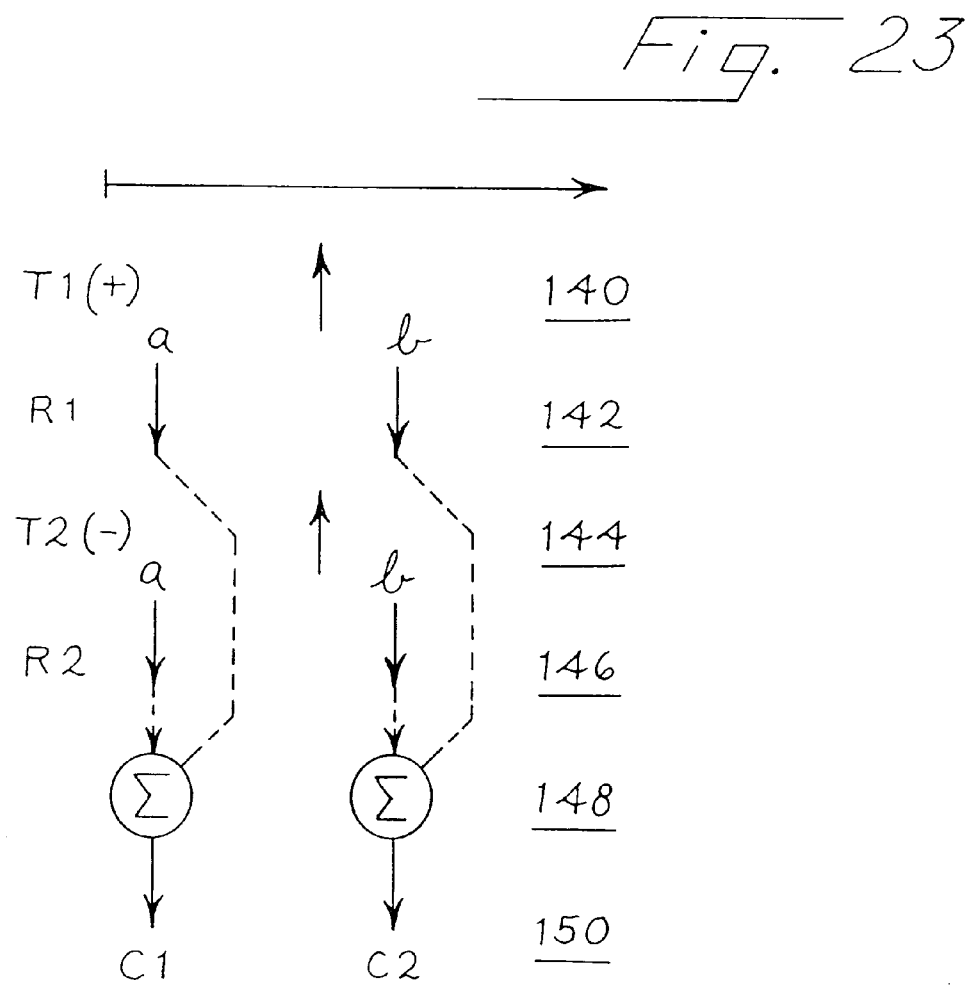
FIG. 23 is a flowchart of an additional embodiment of this invention.

FIG. 23 shows a flowchart of another embodiment of the method of this invention. In the method of FIG. 23, a first transmit beam T1 (positive polarity) is transmitted along a first azimuthal direction in step 140, and in step 142 two spatially distinct receive beams R1a, R1b are received. As shown in FIG. 23, receive beams R1a and R1b are offset on respective sides of the azimuthal direction of the transmit beam T1. In step 144, a second transmit beam T2 (negative polarity) is transmitted along the same azimuthal direction as transmit beam T1, and in step 146 two receive beams R2*a*, R2*b* are received. In this embodiment, receive beams R1*a*, R2*a*, are spatially aligned and receive beams R1*b*, R2*b* are spatially aligned. In step 148, spatially aligned receive beams R1*a*, R2*a* are summed and spatially aligned receive beams R1*b*, R2*b* are separately summed to form composite signals C1, C2 respectively. In step 150 the composite signals C1, C2 are applied to the image processor.

In the method of FIG. 23 two transmit beams are required to generate two composite signals, and therefore the composite signals C1, C2 are acquired with no degradation of temporal resolution or frame rate as compared to conventional single pulse imaging techniques.

Conclusion

Of course, many changes and modifications can be made to the preferred embodiments described above. For example, combinations of the various embodiments described above are possible. In one alternative embodiment, both transmit phase and receive aperture are alternated among beams, using either sequential or simultaneous alternation techniques. For example, in one sequential alternation embodiment left and right receive apertures are alternated with a positive transmit polarity phase over two scan lines, and then left and right receive apertures are alternated with negative transmit polarity phase over the next two scan lines, and all four scan lines are coherently summed to create the composite beam. In one simultaneous alteration technique a positive transmit polarity pulse/left (or inside or even element) receive aperture configuration is alternated with a negative transmit polarity pulse/right (or outside or odd element) receive aperture, and two scan lines are coherently summed to create the composite beam. Simultaneous alteration techniques are preferred for two or more alternating parameters if there is little or no interaction between or among the parameters. In general, the line density controls the resulting performance level and frame rate. In cases where synthetic line features are available with sufficient bandwidths, each of the proposed modes and combinations described above can be programmed to have the same frame rate advantage; however, performance can be improved since common receive lines can be coincident yet multiple coincident transmit lines are avoided to eliminate any unnecessary decrease in the frame rate. This can offer advantages when tissue motion is an issue, as in cardiology applications.

The term "alternate" is therefore intended broadly to encompass alternating sets of n elements, $n \geq 2$. Thus, the term "alternating line" is broad enough to cover every other line, every other group of two lines, and so forth. Also, the term "alternate" is intended broadly to encompass every nth line, $n \geq 2$, and the term "alternating line" therefore encompasses every second line, every third line, and so forth.

In certain of the embodiments described above, selected pre-detection receive beams are coherently combined. Coherent combination is discussed extensively in the above-identified U.S. Pat. No. 5,667,373, assigned to the assignee of this invention, and the entirety of the disclosure of this patent is hereby incorporated by reference for its teaching regarding alternative forms of coherent combination.

The methods described above can be used both in situations where a non-linear contrast agent is introduced into the region of interest as well as in situations where the region of interest is maintained free of added non-linear contrast agent. For example, the methods described above can be used during a medical diagnostic examination session in which the subject is maintained free of added non-linear contrast agent during the entire session. In this case, the harmonic components described above are generated by natural processes associated with the propagation of ultrasound through body tissues.

The systems and methods described above can be implemented using a wide variety of hardware. For example, the transmit beamformer 12 and the receive beamformer 18 can be made to operate using any suitable architecture, including both analog and digital architectures. The beamformers 12, 18 can also be of the simultaneous multi-beam transmit-multi beam receive type, particularly where simultaneous transmit beams are widely spaced.

The transducer array 14 can be a one-dimensional, 1.5 dimensional or 2 dimensional array, flat or curved, and of either constant or varying thickness. The transmit beams can be formed of transmit waveforms of the widest variety of shapes including unipolar and bipolar pulses, with or without smoothly rising and falling envelopes. Sinusoidal, square wave or multi-level square wave techniques can be used. The waveform generator 20 and the focus delay 22 can vary widely in complexity and sophistication. The phase inverter 24 can operate in an analog or digital fashion, and it can be implemented by delays, phase rotations or phase inversions. The controller 26 can be included as part of the transmit beamformer 12; alternately the phase inverter 24 can be implemented separately from the transmit beamformer 12. The controller 26 may control the phase inverter 24 without controlling other elements of the system. The line buffer 28 and the summer 30 can be implemented as analog or digital systems, and the line buffer 28 may correspond to a digital memory for multiple receive beams.

In all of the embodiments discussed above, the receive processing is in the same mode for the receive beams that are associated with spatially distinct transmit lines having differing transmit scan parameters. For example, the receive beams associated with spatially distinct transmit beams of differing transmit parameters can both be processed in a B mode processing mode, in a Doppler processing mode, or in other known processing modes.

All of the techniques described above can be implemented along either the azimuthal dimension or the elevation dimension. Similarly, the alternating line techniques described above can be used in both azimuth and elevation in 3D scanning, as described above in conjunction with FIG. 32. Thus, these techniques are well suited for both two-dimensional (range plus azimuthal or elevation) and three-dimensional imaging. As an example, synthetic aperture techniques can be used in elevation with an articulated one-dimensional array, as described in U.S. patent application Ser. No. 09/282,910, filed Mar. 31, 1999, now U.S. Pat. No. 6,132,375.

The methods described above can be implemented over a full frame of image data or part of a frame, and they can be used with a wide variety of ultrasonic imaging signals including B mode signals, Doppler signals and the like.

The methods described above can also be implemented using M mode techniques, in which a portion of the B mode frame, often a single scan line, is displayed. For example, alternating line techniques can be used to alternate any of the scan parameters discussed above along two adjacent scan lines, and spatially aligned receive beams can then be combined to produce the M mode line.

The methods described above can be implemented using multiple simultaneous transmit beam techniques, with one or more receive beams acquired for each transmit beam.

Though the examples described above emphasize second harmonic components, this invention is not limited to use with second harmonic signals. As used herein, the term "harmonic" is intended broadly to encompass any non-linear echo signal, including sub-harmonics, fractional harmonics and integral harmonics of 2 and greater.

In certain of the embodiments described above, various receive parameters are alternated from line to line. Many alternatives are possible including alternating receive spectral response (e.g., receive center frequency, receive spectral bandwidth, shape of receive spectral response) from line to line. In several of the embodiments described above, it is important to provide coherent combination of receive beams prior to detection. Of course, coherent combination requires adequate control of receive beam phase on a scan-line to scan-line basis. Related U.S. patent application Ser. No. 09/282,511, filed Mar. 31, 1999, provides one preferred technique for achieving the desired phase alignment.

As indicated above, various embodiments of this invention will obtain various degrees of cancellation of the fundamental components by destructive interference in the composite signal. Thus, the term "destructive interference" is intended broadly to encompass both partial and complete interference.

The present invention can be used with any suitable scan line geometry, including sector, Vector®, and parallel beam geometries, for example.

As used herein, the term "scan parameter" is intended broadly to encompass transmit and/or receive parameters other than beam steering direction and beam origin.

The term "spatially distinct" is intended broadly to encompass transmit lines that are spatially distinct in azimuth, in elevation, or both.

With respect to the embodiments described above that utilize transmit beams which are entirely spatially distinct from one another, it may be desirable to fire additional transmit beams which are spatially aligned with previously fired transmit beams.

The foregoing detailed description has discussed only a few of the many forms that this invention can take. It is therefore intended that the foregoing detailed description be regarded as illustrative rather than limiting. It is only the following claims, including all equivalents, that are intended to define the scope of this invention.

What is claimed is:

1. An ultrasonic imaging method comprising the following acts:
    (a) transmitting a set of ultrasonic transmit beams into a region, at least some of the transmit beams focused at spatially distinct directions, said transmit beams each comprising a respective fundamental transmit component, the fundamental transmit components associated with selected ones of the transmit beams characterized by a phase difference;
    (b) receiving a plurality of ultrasonic receive beams from the region, each receive beam associated with a respective one of the transmit beams, and each receive beam comprising a respective fundamental receive component and a respective harmonic receive component;
    (c) summing at least two of the receive beams associated with spatially distinct ones of the transmit beams to form a composite signal, said phase difference of act (a) selected to cause the fundamental receive components to destructively interfere to a greater extent than the harmonic receive components in act (c).

2. The method of claim 1 wherein the transmit beams traverse the region.

3. The method of claim 1 wherein each of the receive beams is spatially aligned with the respective associated transmit beam.

4. The method of claim 1 wherein at least some of the receive beams are spatially offset from the respective associated transmit beams.

5. The method of claim 4 wherein act (b) comprises receiving a respective plurality of the receive beams in association with each transmit beam.

6. The method of claim 1 or 5 wherein the receive beams summed in act (c) are spatially aligned.

7. The method of claim 1 wherein the receive beams summed in act (c) are spatially distinct.

8. The method of claim 1 wherein act (b) comprises receiving two of the receive beams in association with each of the transmit beams, and wherein the receive beams summed in act (c) are spatially aligned.

9. The method of claim 1 wherein the phase difference approaches 180°.

10. The method of claim 1 further comprising introducing a non-linear contrast agent into the region prior to act (a).

11. The method of claim 1 wherein acts (a)–(c) are performed during a medical diagnostic examination session, and further comprising maintaining the region free of added non-linear contrast agent during the entire medical diagnostic examination session.

12. The method of claim wherein act (c) comprises coherently summing said at least two of the receive beams to form the composite signal.

13. The method of claim 1 wherein the transmit beams are spaced at a selected range to provide Nyquist sampling.

14. The method of claim 1 wherein the transmit beams are spaced at a selected range by a separation $S_B$ greater than a separation $S_N$ required for Nyquist sampling.

15. The method of claim 1 wherein the transmit beams are spaced at a selected range by a separation $S_B$ less than a separation $S_N$ required for Nyquist sampling, and wherein $S_B/S_N$ is no less than ½.

16. The method of claim 1 wherein the transmit beams are spaced at a selected range by a separation $S_B$ less than a separation $S_N$ required for Nyquist sampling, and wherein $S_B/S_N$ is less than ½.

17. The method of claims 13, 14, 15 or 16 wherein the transmit beams are characterized by a transmit focal range and wherein the selected range is at the transmit focal range.

18. The method of claims 13, 14, 15 or 16 wherein the transmit beams are characterized by a transmit focal range, and wherein the selected range is spaced from the transmit focal range.

19. The method of claim 1 wherein act (a) comprises inverting a phase of the fundamental transmit components for alternate ones of the transmit beams such that the phase difference is about equal to 180°.

20. In an ultrasonic imaging system comprising:
    a transducer array;
    a transmit beamformer coupled to the transducer array and operative to transmit a set of ultrasonic transmit beams into a region, said transmit beams focused at spatially distinct directions, said transmit beams each comprising a respective fundamental transmit component;
    a controller coupled to the transmit beamformer and operative to cause the fundamental transmit components associated with selected ones of the transmit beams to differ from one another by a selected phase difference;
    a receive beamformer coupled to the transducer array and operative to receive a plurality of receive beams from the region, each receive beam associated with a respective one of the transmit beams, and each receive beam comprising a respective fundamental receive component and a respective harmonic receive component;

a summer operative to sum at least two of the receive beams associated with spatially distinct ones of the transmit beams to form a composite signal, said phase difference effective to cause the fundamental receive components to destructively interfere to a greater extent than the harmonic receive components in the composite signal.

21. The method of claim 20 wherein the transmit beams traverse the region.

22. The method of claim 20 wherein each of the receive beams is spatially aligned with the respective associated transmit beam.

23. The method of claim 20 wherein at least some of the receive beams are spatially offset from the respective associated transmit beams.

24. The method of claim 20 wherein the receive beamformer is operative to receive a respective plurality of the receive beams in association with each transmit beam.

25. The invention of claim 20 or 24 wherein the receive beams summed in the summer are spatially aligned.

26. The invention of claim 20 wherein the receive beams summed in the summer are spatially distinct.

27. The invention of claim 20 wherein the phase difference approaches 180°.

28. The invention of claim 20 wherein the summer is operative to coherently sum said at least two of the receive beams to form the composite signal.

29. The method of claim 20 wherein the transmit beams are spaced at a selected range to provide Nyquist sampling.

30. The method of claim 20 wherein the transmit beams are spaced at a selected range by a separation $S_B$ greater than a separation $S_N$ required for Nyquist sampling.

31. The method of claim 20 wherein the transmit beams are spaced at a selected range by a separation $S_B$ less than a separation $S_N$ required for Nyquist sampling, and wherein $S_B/S_N$ is no less than ½.

32. The method of claim 20 wherein the transmit beams are spaced at a selected range are spaced by a separation $S_B$ less than a separation $S_N$ required for Nyquist sampling, and wherein $S_B/S_N$ is less than ½.

33. The method of claim 29, 30, 31 or 32 wherein the transmit beams are characterized by a transmit focal range, and wherein the selected range is at the transmit focal range.

34. The method of claim 29, 30, 31 or 32 wherein the transmit beams are characterized by a transmit focal range, and wherein the selected range is spaced from the transmit focal range.

35. The invention of claim 20 wherein the transmit beamformer comprises an inverter, responsive to the controller, operative to invert a phase of the fundamental transmit components for alternate ones of the transmit beams such that the phase difference is about equal to 180°.

36. An ultrasonic imaging method comprising the following acts:

(a) transmitting a set of ultrasonic transmit beams into a region, said transmit beams each comprising a respective fundamental transmit component, the fundamental transmit components associated with selected ones of the transmit beams characterized by a phase difference;

(b) receiving a plurality of ultrasonic receive beams from the region, at least two of the receive beams associated with each respective one of the transmit beams, each receive beam comprising a respective fundamental receive component and a respective harmonic receive component;

(c) summing at least two of the receive beams to form a composite signal, said phase difference effective to cause the fundamental receive components to destructively interfere to a greater extent than the harmonic receive components in act (c).

37. The method of claim 36 wherein the receive beams summed in act (c) are spatially aligned.

38. The method of claim 36 wherein at least some of the receive beams summed in act (c) are spatially distinct.

39. The method of claim 36 or 37 wherein the transmit beams associated with the receive beams summed in act (c) are spatially aligned.

40. The method of claim 36 or 37 wherein the transmit beams associated with the receive beams summed in act (c) are spatially distinct.

41. An ultrasonic imaging system comprising:

a transducer array;

a transmit beamformer coupled to the transducer array and operative to transmit a set of ultrasonic transmit beams into a region, said transmit beams each comprising a respective fundamental transmit component;

a controller coupled to the transmit beamformer and operative to cause the fundamental transmit components associated with selected ones of the transmit beams to differ from one another by a selected phase difference;

a receive beamformer coupled to the transducer array and operative to receive a plurality of receive beams from the region in response to each respective one of the transmit beams, each receive beam comprising a respective fundamental receive component and a respective harmonic receive component;

a summer operative to sum at least two of the receive beams to form a composite signal, said phase difference effective to cause the fundamental receive components to destructively interfere to a greater extent than the harmonic receive components in the composite signal.

42. The invention of claim 41 wherein the receive beamformer is operative to receive the receive beams summed by the summer as spatially aligned receive beams.

43. The invention of claim 41 or 42 wherein the transmit beamformer is operative to transmit the transmit beams associated with the receive beams summed by the summer as spatially aligned transmit beams.

44. The invention of claim 41 or 42 wherein the transmit beamformer is operative to transmit the transmit beams associated with the receive beams summed by the summer as spatially distinct transmit beams.

45. The invention of claim 41 wherein the receive beamformer is operative to receive at least some of the receive beams summed by the summer as spatially distinct receive beams.

46. An ultrasonic imaging method comprising the following acts:

(a) transmitting a set of ultrasonic transmit beams into a region, said transmit beams each comprising a respective fundamental transmit component, the fundamental transmit components associated with selected ones of the transmit beams characterized by a phase difference;

(b) receiving a plurality of ultrasonic receive beams from the region, each receive beam associated with a respective one of the transmit beams, and each receive beam comprising a respective fundamental receive component and a respective harmonic receive component;

(c) summing at least two spatially distinct ones of the receive beams to form a composite signal, said phase difference effective to cause the fundamental receive components to destructively interfere to a greater extent than the harmonic receive components in act (c).

47. The method of claim 46 wherein three of the receive beams are summed in act (c).

48. The method of claim 46 wherein four of the receive beams are summed in act (c).

49. An ultrasonic imaging system comprising:
a transducer array;
a transmit beamformer coupled to the transducer array and operative to transmit a set of ultrasonic transmit beams into a region, said transmit beams each comprising a respective fundamental transmit component;
a controller coupled to the transmit beamformer and operative to cause the fundamental transmit components associated with selected ones of the transmit beams to differ from one another by a selected phase difference;
a receive beamformer coupled to the transducer array and operative to receive a plurality of receive beams from the region in response to the transmit beams, each receive beam comprising a respective fundamental receive component and a respective harmonic receive component;
a summer operative to sum at least two spatially distinct ones of the receive beams to form a composite signal, said phase difference effective to cause the fundamental receive components to destructively interfere to a greater extent than the harmonic receive components in the composite signal.

50. The invention of claim 49 wherein the summer is operative to sum three of the receive beams.

51. The invention of claim 49 wherein the summer is operative to sum four of the receive beams.

52. An ultrasonic imaging method comprising the following acts:
(a) transmitting a set of ultrasonic transmit beams into a region, said transmit beams each comprising a respective fundamental transmit component, the fundamental transmit components associated with selected ones of the transmit beams characterized by a phase difference;
(b) receiving a plurality of ultrasonic receive beams from the region, each receive beam associated with a respective one of the transmit beams, and each receive beam comprising a respective fundamental receive component and a respective harmonic receive component;
(c) summing at least three of the receive beams using at least two different summing weights to form a composite signal, said phase difference effective to cause the fundamental receive components to destructively interfere to a greater extent than the harmonic receive components in act (c);
wherein at least some of the summed receive beams are selected from the group consisting of receive beams that are spatially distinct, and receive beams that are associated with spatially distinct transmit beams.

53. An ultrasonic imaging method comprising the following acts:
(a) transmitting a set of ultrasonic transmit beams into a region, said transmit beams each comprising a respective fundamental transmit component, the fundamental transmit components associated with selected ones of the transmit beams characterized by a phase difference;
(b) receiving a plurality of ultrasonic receive beams from the region, each receive beam associated with a respective one of the transmit beams, and each receive beam comprising a respective fundamental receive component and a respective harmonic receive component;
(c) summing an odd number of the receive beams to form a composite signal, said phase difference effective to cause the fundamental receive components to destructively interfere to a greater extent than the harmonic receive components in act (c);
wherein at least some of the summed receive beams are selected from the group consisting of receive beams that are spatially distinct, and receive beams that are associated with spatially distinct transmit beams.

54. The method of claim 53 wherein the odd number is three.

55. The method of claim 52 or 53 wherein at least some of the summed receive beams are spatially distinct.

56. The method of claim 52 or 53 wherein at least some of the summed receive beams are associated with spatially distinct transmit beams.

57. An ultrasonic imaging system comprising:
a transducer array;
a transmit beamformer coupled to the transducer array and operative to transmit a set of ultrasonic transmit beams into a region, said transmit beams each comprising a respective fundamental transmit component;
a controller coupled to the transmit beamformer and operative to cause the fundamental transmit components associated with selected ones of the transmit beams to differ from one another by a selected phase difference;
a receive beamformer coupled to the transducer array and operative to receive a plurality of receive beams from the region in response to the transmit beams, each receive beam comprising a respective fundamental receive component and a respective harmonic receive component;
a summer operative to sum at least three of the receive beams using at least two different summing weights to form a composite signal, said phase difference effective to cause the fundamental receive components to destructively interfere to a greater extent than the harmonic receive components in the composite signal;
wherein at least some of the summed receive beams are selected from the group consisting of receive beams that are spatially distinct, and receive beams that are associated with spatially distinct transmit beams.

58. An ultrasonic imaging system comprising:
a transducer array;
a transmit beamformer coupled to the transducer array and operative to transmit a set of ultrasonic transmit beams into a region, said transmit beams each comprising a respective fundamental transmit component;
a controller coupled to the transmit beamformer and operative to cause the fundamental transmit components associated with selected ones of the transmit beams to differ from one another by a selected phase difference;
a receive beamformer coupled to the transducer array and operative to receive a plurality of receive beams from the region in response to the transmit beams, each receive beam comprising a respective fundamental receive component and a respective harmonic receive component;

a summer operative to sum an odd number of receive beams to form a composite signal, said phase difference effective to cause the fundamental receive components to destructively interfere to a greater extent than the harmonic receive components in the composite signal;

wherein at least some of the summed receive beams are selected from the group consisting of receive beams that are spatially distinct, and receive beams that are associated with spatially distinct transmit beams.

59. The invention of claim 58 wherein the odd number is three.

60. The invention of claim 52 or 53 wherein at least some of the summed receive beams are spatially distinct.

61. The invention of claim 57 or 58 wherein at least some of the summed receive beams are associated with spatially distinct transmit beams.

* * * * *

UNITED STATES PATENT AND TRADEMARK OFFICE
CERTIFICATE OF CORRECTION

PATENT NO. : 6,193,663 B1
DATED : February 27, 2001
INVENTOR(S) : David J. Napolitano et al.

It is certified that error appears in the above-identified patent and that said Letters Patent is hereby corrected as shown below:

Column 4,
Line 52, delete "24" and substitute -- 2-4 -- in its place.

Column 10,
Line 32, delete "ok" and substitute -- $\theta_k$ -- in its place.

Column 12,
Line 47, delete "T1 a" and substitute -- T1$a$ -- in its place.

Column 13,
Line 1, delete "(+-)" and substitute -- (+-) -- in its place.

Lines 3, 4 and 5, delete "(-+)" and substitute -- (-+) -- in its place.

Line 52, delete "code I" and substitute -- code 1 -- in its place.

Column 16,
Line 11, delete "multi beam" and substitute -- multi-beam -- in its place.

Column 18,
Line 24, delete "claim" and substitute -- claim 1 -- in its place.

Column 24,
Line 3, delete "claims 52 or 53" and substitute -- claims 57 or 58 -- in its place.

Signed and Sealed this

Nineteenth Day of November, 2002

Attest:

*Attesting Officer*

JAMES E. ROGAN
*Director of the United States Patent and Trademark Office*